US009521850B2

(12) United States Patent
Wang et al.

(10) Patent No.: US 9,521,850 B2
(45) Date of Patent: *Dec. 20, 2016

(54) ANTIMICROBIAL COMPOUNDS AND THEIR USE IN TREATING PLANT DISEASE

(71) Applicant: University of Florida Research Foundation, Incorporated, Gainesville, FL (US)

(72) Inventors: Nian Wang, Lake Alfred, FL (US); Nagaraju Akula, Lake Alfred, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/957,645

(22) Filed: Dec. 3, 2015

(65) Prior Publication Data

US 2016/0081341 A1 Mar. 24, 2016

Related U.S. Application Data

(63) Continuation of application No. 14/498,454, filed on Sep. 26, 2014, now Pat. No. 9,247,749, which is a continuation-in-part of application No. PCT/US2013/033871, filed on Mar. 26, 2013.

(60) Provisional application No. 61/615,555, filed on Mar. 26, 2012.

(51) Int. Cl.

| | |
|---|---|
| *A01N 43/90* | (2006.01) |
| *A01N 25/00* | (2006.01) |
| *A01N 43/48* | (2006.01) |
| *A01N 43/62* | (2006.01) |
| *A01N 43/713* | (2006.01) |
| *A01N 43/78* | (2006.01) |
| *C05G 3/02* | (2006.01) |

(52) U.S. Cl.

CPC ............... *A01N 43/90* (2013.01); *A01N 25/00* (2013.01); *A01N 43/48* (2013.01); *A01N 43/62* (2013.01); *A01N 43/713* (2013.01); *A01N 43/78* (2013.01); *C05G 3/02* (2013.01)

(58) Field of Classification Search

None

See application file for complete search history.

(56) References Cited

U.S. PATENT DOCUMENTS

| | | | | |
|---|---|---|---|---|
| 9,247,749 | B2 * | 2/2016 | Wang ..................... | A01N 43/62 |
| 2004/0009972 | A1 | 1/2004 | Ding et al. | |
| 2004/0170978 | A1 | 9/2004 | Schmidt et al. | |
| 2005/0272723 | A1 | 12/2005 | Glick | |
| 2010/0093747 | A1 * | 4/2010 | Goodhew .......... | A61K 31/4184 514/252.06 |

OTHER PUBLICATIONS

Shestopalov et al.(Cyclization of nitriles. XI. Syntheses from 2-aryl-3-aroyl-1,1-dicyanopropanes, Zhurnal Organicheskoi Khimii, 1984, 20(7), 1517-38). ABS.*

Akula, Nagaraju et al., "Discovery of novel SecA inhibitors of *Candidatus* Liberibacter asiaticus by structure based design," *Bioorganic & Medical Chemistry Letters*, 2001, 21:4183-4188.

Andrews, Jennifer M. "Determination of minimum inhibitory concentrations," *Journal of Antimicrobial Chemotherapy*, 2001, *Suppl S1*, 48:5-16.

Barloy-Hubler, Frédérique et al., "Smc01944, a secreted peroxidase induced by oxidative stresses in *Sinorhizobium meliloti* 1021", *Microbiology*, 2004, 150:657-664.

Bovë, J.M. "Huanglongbing: A Destructive, Newly-Emerging, Century-Old Disease of Citrus," *Journal of Plant Pathology*, 2006, 88(1):7-37.

Chen, Weixuan et al., "The first low μM SecA inhibitors," *Bioorganic & Medicinal Chemistry*, 2010, 18:1617-1625.

Chilton, Mary-Dell et al., "*Agrobacterium tumefaciens* DNA and PS8 Bacteriophage DNA Not Detected in Crown Gall Tumors," *Proceedings of the National Academy of Sciences*, Sep. 1974, 71(9):3672-3676.

Dombrecht, Bruno et al., "Defence of *Rhizobium etli* bacteroids against oxidative stress involves a complexly regulated atypical 2-Cys peroxiredoxin," *Molecular Microbiology*, 2005, 55(4):1207-1221.

Duan, Yongping et al., "Complete Genome Sequence of Citrus Huanglongbing Bacterium, '*Candidatus* Liberibacter asiaticus' Obtained Through Metagenomics," *Molecular Plant-Microbe Interactions Journal*, 2009, 22(8):1011-1020.

Economou, A. et al., "SecA promotes preprotein translocation by undergoing ATP-driven cycles of membrane insertion and deinsertion," *Cell*, Sep. 1994, 78(5):835-843.

Fagen, Jennie R. et al., "Comparative Genomics of Cultured and Uncultured Strains Suggests Genes Essential for Free-Living Growth of *Liberibacter," PLoS One*, Jan. 2014, 9(1):1-11.

Friesner, Richard A. et al., "Glide: A New Approach for Rapid, Accurate Docking and Scoring. 1. Method and Assessment of Docking Accuracy," *Journal of Medicinal Chemistry*, 2004, 47(7):1739-1749.

Gelis, Ioannis et al., "Structural Basis for Signal-Sequence Recognition by the Translocase Motor SecA as Determined by NMR," *Cell*, Nov. 16, 2007, 131:756-769.

Gottwald, Tim R. et al., "Current Epidemiological Understanding of Citrus Huanglongbing*," *Annual Review of Phytopathology*, 2010, 48:119-139.

Da Graça, J. V., "Citrus Greening Disease," *Annual Review of Phytopathology*, 1991, 29:109-136.

Halbert, Susan E. et al., "Asian Citrus Psyllids Sternorrhyncha: Psyllidae) and Greening Disease of Citrus: A Literature Review and Assessment of Risk in Florida," *Florida Entomologist*, 2004, 87(3):330-353.

Hanyu, Masaki et al., "Functional Differences of Two Distinct Catalases in *Mesorhizobium loti* MAFF303099 under Free-Living and Symbiotic Conditions," *Journal of Bacteriology*, 2009, 191(5):1463-1471.

Henkel, R.D. et al., "A microassay for ATPase," *Analytical Biochemistry*, Mar. 1988, 169(2): Abstract.

Huang, Ying-Ju. "Characterization of Structure and Function of SECA Domains," *Biology Dissertations*, 2011, Abstract.

(Continued)

*Primary Examiner* — Alton Pryor

(74) *Attorney, Agent, or Firm* — Saliwanchik, Lloyd & Eisenschenk

(57) ABSTRACT

The subject invention is directed toward antimicrobial agents and methods of treating and preventing infection by pathogenic microorganisms and endophytic microorganisms in a plant through the use of SecA inhibitors.

28 Claims, 6 Drawing Sheets

(56) References Cited

OTHER PUBLICATIONS

Irwin, John J. et al., "ZINC—A Free Database of Commercially Available Compounds for Virtual Screening," *Journal of Chemical Information and Modeling*, 2005, 45(1):177-182.

Jang, M.Y. et al., "Synthesis of novel 5-amino-thiazolo[4,5-d]pyrimidines as *E. coli* and *S. aureus* SecA inhibitors," *Bioorganic and Medical Chemistry*, Jan. 2011, 19(1):Abstract.

Jin, Jinshan. "Characterization of SecA1 and SecA2 from Gram-Positive Pathogens and Discovery of Novel SecA Inhibitors," *Biology Disseratations*, 2001, Abstract.

Jorgensen, James H. et al., "Antimicrobial Susceptibility Testing: A Review of General Principles and Contemporary Practices," *Medical Microbiology*, Dec. 2009, 49:1749-1755.

Jorgensen, William L. et al., "Development and Testing of the OPLS All-Atom Force Field on Conformational Energetics and Properties of Organic Liquids," *Journal of the American Chemical Society*, 1996, 118:11225-11236.

Lebel, Denis et al., "A Convenient Method for the ATPase Assay," *Analytical Biochemistry*, Mar. 1978, 85(1):Abstract.

Leonard, Michael T. et al., "Complete genome sequence *Liberibacter crescens* BT-1" *Standards in Genomic Sciences*, 2012, 7:271-283.

Lin, Hong et al., "The Complete Genome Sequence of '*Candidatus* Liberibacter solanacearum', the Bacterium Associated with Potato Zebra Chip Disease," *PLoS ONE*, Apr. 2011, 6(4):1-13.

Lin, Hsiu-Li et al., "Revisiting with a Relative-Density Calibration Approach the Determination of Growth Rates of Microorganisms by Use of Optical Density Data from Liquid Cultures," *Applied and Environmental Microbiology*, 2010, 76(5):1683-1685.

Li, Minyong et al., "Discovery of the first SecA inhibitors using structure-based virtual screening," *Biochemical and Biophysical Research Communication*, 2008, 368:839-845.

Manting, Erik H. et al., "*Escherichia coli* translocase: the unravelling of a molecular machine," *Molecular Microbiology*, 2000, 37(2):226-238.

Mohamadi, Fariborz et al., "Macromodel—an integrated software system for modeling organic and bioorganic molecules using molecular mechanics," *Journal of Computational Chemistry*, May 1990, 11(4):440-467.

Papanikolau, Yannis et al., "Structure of Dimeric SecA, the *Escherichia coli* Preprotein Translocase Motor," *Journal of Molecular Biology*, 2006, Article in Press, pp. 1-35.

Sagaram, Uma Shankar et al., "Bacterial Diversity Analysis of Huanglongbing Pathogen-Infected Citrus using PhyloChips and 16S rDNA Clone Library Sequencing," *Department of Microbiology and Cell Science*, 2009, 75:1566-1574.

Sechler, A. et al., "Cultivation of '*Candidatus* Liberibacter asiaticus', '*Ca.* L. africanus,' and '*Ca.* L. americanus' Associated with Huanglongbing," *Phytopathology*, 2009, 99(5):480-486.

Segers, Kenneth et al., "Traffic Jam at the Bacterial Sec Translocase: Targeting the SecA Nanomotor by Small-Molecule Inhibitors," *Chemistry & Biology Review*, Jun. 2011, 18:685-698.

Shah, Ritu et al., "Isocitrate Dehydrogenase of *Bradyrhizobiurn japonicum* is Not Required for Symbiotic Nitrogen Fixation with Soybean," *Journal of Bacteriology*, 2006, 188(21):7600-7608.

Silva, I.C. et al., "Antibacterial Activity of Alkyl Gallates Against Xanthomonas citri subsp. *citri," Journal of Bacteriology*, 2013, 195(1):85-94.

Taylor, P.C. et al., "Determination of Minimum Bactericidal Concentrations of Oxacillin for *Staphylococcus aureus*: Influence and significance of Technical Factors," *Antimicrobial Agents and Chemotherapy*, 1983, 23(1):142-150.

Trivedi, Pankaj et al., "Isolation and Characterization of Beneficial Bacteria Associated with Citrus Roots in Florida," *Microbial Ecology Journal*, 2011, 62:324-336.

Vahling, Cheryl M. et al., "Characterization of an ATP Translocase Identified in the Destructive Plant Pathogen *Candidatus* Liberibacter asiaticus," *Journal of Bacteriology*, Feb. 2010, 192(3):834-840.

Van Den Berg, Bert et al., "X-ray structure of a protein-conducting channel," *Nature*, Jan. 2004, 427:36-44.

Vojnov, Adrián Alberto et al., "Bacteria causing important disease of citrus utilise distinct modes of pathogenesis to attack a common host," *Applied Microbial Biotechnology*, 2010, 87:467-477.

Wallace, R.J. et al., "Susceptibility testing of slowly growing mycobacteria by a microdilution MIC method with 7H9 broth," *Journal of Clinical Microbiology*, 1986, 24(6):976-981.

Wang, Nian. "Control of Citrus Huanglongbing by disruption of the transmission of citrus greening pathogen by psyllids," *Citrus Advanced Technology Program*, Aug. 20, 2010.

Wang, Nian. "Control of Citrus Huanglongbing by disruption of the transmission of citrus greening pathogen by psyllids," *Citrus Advanced Technology Program*, Oct. 6, 2011.

Wang, Nian. "Control of Citrus Huanglongbing by disruption of the transmission of citrus greening pathogen by psyllids," *Citrus Advanced Technology Program*, 2011, Jan. 14, 2011.

Zhang, Muqing et al., "Chemical Compounds Effective against the Citrus Huanglongbing Bacterium '*Candidatus* Liberibacter asiaticus' In Planta," *Phytopathology*, 2011, 101(9):1097-1103.

Zhang, Muqing et al., "Screening Molecules for Control of Citrus Huanglongbing Using an Optimized Regeneration System for '*Candidatus* Liberibacter asiaticus'—Infected Periwinkle (*Catharanthus roseus*) Cuttings," *Phytopathology*, 2010, 100(3):239-245.

Delano, Warren L. "PyMOL: An Open-Source Molecular Graphics Tool," accessed from http://www.pymol.org/, DeLano Scientific, San Carlos, California, USA, 2002.

Liang, Jun et al., "Ecological Control of Forest Pest: A New Strategy for Forest Pest Control," *Journal of Forestry Research*, Dec. 2005, 16(4):Abstract.

Schrödinger, LLC, "Induced Fit: A novel method for fast and accurate prediction of ligand induced conformational changes in receptor active sites," accessed from http://www.schrodinger.com/Induced-Fit/2005, Oct. 12, 2005, pp. 1-2.

* cited by examiner (C1)

(C2)

(C3)

(C4)

(C5)

(C6)

(C7)

(C8)

(C9)

(C10)

(C11)

(C12)

(C13)

(C14)

(C15)

(C16)

(C17)

(C18)

(C19)

(C20)

ANTIMICROBIAL COMPOUNDS AND THEIR USE IN TREATING PLANT DISEASE

CROSS-REFERENCE TO RELATED APPLICATIONS

This application is a continuation application of U.S. Ser. No. 14/498,454, filed Sep. 26, 2014; which is a continuation-in-part of International Patent Application No. PCT/US2013/0338710, filed Mar. 26, 2013; which claims the benefit of U.S. Provisional Application No. 61/615,555, filed on Mar. 23, 2012, all of which are incorporated herein by reference in their entirety.

BACKGROUND OF INVENTION

Bacterial plant pathogens pose unique problems for disease control. One primary control strategy for bacterial diseases is based on excluding the pathogen through the use of disease free seed, or quarantine and eradication if bacterial pathogens are introduced into an area.

There are only a few chemical control agents for established bacterial diseases, and their use is often limited because of phytotoxicity or pathogen mutations resulting in resistance to the agent. Also, commonly applied protective copper compounds (for example sulfates or oxides) have limited benefit in controlling bacterial diseases because of their poor penetration into plant tissues where bacteria establish themselves and, again, mutations provide bacteria with resistance to these materials.

Unlike the control of disease outbreaks in annual crops that can be remediated in subsequent years through sanitation and the use of bacteria-free seed stocks, replanting of perennial crops such as citrus involves high capital costs to establish the planting, and several years after planting before production is initiated.

Established bacterial diseases such as those caused by *Candidatus liberibacter* species (citrus greening or Huanglongbing, psyllid yellows and tomato, or purple top and zebra chip of potatoes, etc.) that survive in alternate host plants in the environment and are disseminated by insect vectors that commonly infect throughout the plant life cycle are very difficult to contain because of the wide dissemination range of the insect vector and the long lag time for symptom expression (Bove, J. M. (2006) Huanglongbing: a destructive, newly-emerging, century-old disease of citrus. *Journal of Plant Pathology* 88:7-37.). Unfortunately, recent attempts to culture the organism were met with limited success (Sechler, A., Schuenzel, E. L., Cooke, P., Donnua, S., Thaveechai, N., Postnikova, E., Stone, A. L., Schneider, W. L., Damsteegt, V. D. and Schaad, N. W. (2009). Cultivation of '*Candidatus Liberibacter asiaticus*', '*Ca. L. africanus*', and '*Ca. L. americanus*' associated with Huanglongbing. Phytopathology 99, 480-486).

Huanglongbing (HLB) disease (also known as citrus greening or yellow dragon disease) is one such disease associated with the fastidious, Gram-negative, phloem-limited bacterial pathogen, *Candidatus liberibacter* spp. (Las). It is the most destructive citrus disease worldwide (da Graca, J. V. (1991). Citrus greening disease. Ann. Rev. Phytopathol. 29, 109-136; Halbert, S. E., and Manjunath, K. L. (2004). Asian citrus psyllids (Sternorrhyncha: Psyllidae) and greening disease of citrus: A literature review and assessment of risk in Florida. Fla. Entomol. 87, 330-353; and Gottwald, T. R. (2010). Current epidemiological understanding of citrus Haunglongbing. Ann. Rev. Phytopathol. 48, 119-139). The current management strategy of HLB is to chemically control psyllids and scout for and remove infected trees. However, current management practices have not been able to stop the spread of HLB disease (Duan, Y., Zhou, L., Hall, D. G., Li, W., Doddapaneni, H., Lin, H., Liu, L., Vahling, C. M., Gabriel, D. W., Williams, K. P., Dickerman, A., Sun, Y. and Gottwald, T. (2009). Complete genome sequence of citrus huanglongbing bacterium, '*Candidatus Liberibacter asiaticus*' obtained through metagenomics. Mol. Plant Microbe Interact. 22, 1011-1020).

*Candidatus liberibacter* species plug the plant's vascular (phloem) tissues to limit nutrient movement. Symptoms of this disease reflect a severe deficiency of essential mineral nutrients (for example copper, manganese, zinc). A temporary masking of symptoms can be achieved by applying high rates of foliar nutrients; however, the bacterial pathogen remains active and infected trees continue to decline in over-all vigor and productivity. The lag time from infection to symptom expression for this disease varies from six months to five years depending on the age of the tree, vigor, and environmental factors (Bove (2006) *J Plant Pathology* 88:7-37). This lag in symptom expression provides ample time for infection before detection and containment in a new area can be accomplished.

The efficacy of current strategies for management of HLB is limited and no conventional measure has shown to provide consistent and effective suppression of the disease. High cost of frequent insect control and tree removal will eventually render citrus groves unprofitable. In addition, large scale application of insecticides will disrupt the ecosystem and pollute the environment (Jun, L. and Xing-Vao. J. (2005). Ecological control of forest pest: a new strategy for forest pest control. J. Forestry Res. 16, 339-342). Frequently, insecticides will become non-effective due to the acquisition of resistance. Insecticides could also kill non-target beneficial insects which disrupt the biological control currently in place.

Antibiotics injected into the tree's vascular system are often toxic to the tree, and previously available surface-applied copper compounds are not mobile enough to inhibit bacterial activity within vascular or other plant tissues. Current HLB control strategies of frequent insecticide sprays to limit populations of the psyllid insect vector, removal of infected trees, and nutrient maintenance to keep existing trees as productive as possible until they die provide little confidence for a sustainable citrus industry or incentive to reestablish it (Bove (2006) *J Plant Pathology* 88:7-37; UF/IFAS SWFREC, IMMOKALEE IRREC Seminar, 5 Jun. 2009).

Prokaryotes and eukaryotes have evolved numerous systems for the active export of proteins across membranes. In bacteria, the most common form of secretion of peptides with a signal sequence involves the Sec system. SecA is a protein translocase ATPase subunit that is involved in preprotein translocation across and integration into the cellular membrane in bacteria. It is one essential component of the Sec machinery which provides a major pathway of protein translocation from the cytosol across or into the cytoplasmic membrane (Manting, E. H., and Driessen, A. J. (2000). *Escherichia coli* translocase: the unravelling of a molecular machine. Mol. Microbiol. 37, 226-238). Thus, SecA is a promising antimicrobial agent because it is a protein conserved and essential in all bacteria and is absent in humans (Chen, W., Huang. Y. J., Gundala, S. R., Yang, H., Li, M., Tai, P. C. and Wang, B. (2010). The first low microM SecA inhibitors. Bioorg. Med. Chem. 18, 1617-1625; Li, M., Tai, P. C., and Wang, B. (2008). Discovery of the first SecA inhibitors using structure-based virtual screening. Biochem.

Biophys. Res. Commun. 368, 839-845; and Jang, M. Y., De Jonghe, S., Segers, K., Anné, J., Herdewijn, P. (2011). Synthesis of novel 5-amino-thiazolo[4,5-d]pyrimidines as *E. coli* and *S. aureus* SecA inhibitors. Bioorg. Med. Chem. 19, 702).

SecA cooperates with the SecB chaperone to target pre-proteins to SecYEG as an active ATPase gene to drive protein translocation across the bacterial membrane when it is bound to the SecYEG complex (Economou, A., and Wickner, W. (1994). SecA promotes preprotein translocation by undergoing ATP-driven cycles of membrane insertion and deinsertion. Cell. 78, 835-843). SecA is the peripheral membrane ATPase, which couples the hydrolysis of ATP to the stepwise translocation of pre-proteins (Van den Berg, B., Clemons, W. M. J., Collinson, I., Modis, Y., Hartmann, E., Harrison, S. C., and Rapoport, T. A. (2004). X-ray structure of a protein-conducting channel. Nature. 427, 36-44). The crystal structures of SecA are available for other bacteria such as *Escherichia coli* (Papanikolau, Y., Papadovasilaki, M., Ravelli, R. B., McCarthy, A. A., Cusack, S., Economou, A., Petratos, K. (2007). Structure of dimeric SecA, the *Escherichia coli* preprotein translocase motor. J. Mol. Biol. 366, 1545-1557) and the ATPase active site has been clearly defined. This structural information had been utilized for structure based design to identify antimicrobial compounds with $IC_{50}$ value up to 2.5 μM against SecA of *Ca. L. asiaticus* (Akula, N., Zheng, H., Han, F. Q., Wang, N. (2011). Discovery of novel SecA inhibitors of *Candidatus Liberibacter asiaticus* by structure based design. Bioorg. Med. Chem. Lett. 15, 4183-4188).

Development of alternative or complementary approaches for effective management of the disease is highly desirable and will greatly help the citrus industry due to the difficulty to control the HLB disease. Considering the highly destructive nature of HLB disease and the lack of control measures, there is a huge potential to develop antimicrobial small molecules against the causal agent thus to suppress the population of *Ca. L. asiaticus* in plants and to reduce the inoculum for psyllid transmission. Development of antimicrobial small molecules may provide economic and ecological benefits by reducing producing costs, decreasing insecticide application, preserving the natural habitat and populations of beneficial insects, and enhancing productivity of citrus in the presence of HLB.

There is thus a need for antimicrobials that (i) are not subject to the types of antibiotic resistance currently hampering antibiotic treatment of bacteria, (ii) can be developed rapidly and with some reasonable degree of predictability as to target-bacteria specificity, (iii) are effective at low doses, meaning, in part, that they are efficiently taken up by wild-type bacteria or even bacteria that have reduced permeability for antibiotics, and (iv) show few side effects. In particular, there is currently a need in the art for an effective antimicrobial compound to target *Ca. L. asiaticus.*

BRIEF SUMMARY

The present invention provides novel compositions and methods for improving plant health and controlling phytopathogenic bacteria and endophytic microorganisms on or within plant tissue.

The subject invention provides antimicrobial compounds that interrupt, in bacteria, the ATP-hydrolysis process in a Sec system and disrupt pre-protein translocation. In one embodiment, SecA inhibitors are provided that interfere with the ATP binding pocket of SecA, thus affecting protein translocation, including potential signal peptide dependent virulence factors. In a specific embodiment, the SecA inhibitors affect protein translocation and potential signal peptide dependent virulence factors of *Ca. L. asiaticus.*

In accordance with the subject invention, SecA inhibitors are administered to plants to contact bacteria. In one embodiment, an SecA inhibitor is directly injected into the plant vascular system.

The compounds of the invention can be used against bacterial diseases of annual as well as perennial crops and ornamental plants. In preferred embodiments, the SecA inhibitors are particularly effective against *Ca. L. asiaticus* in citrus plants.

DETAILED DISCLOSURE

Figure 1A:
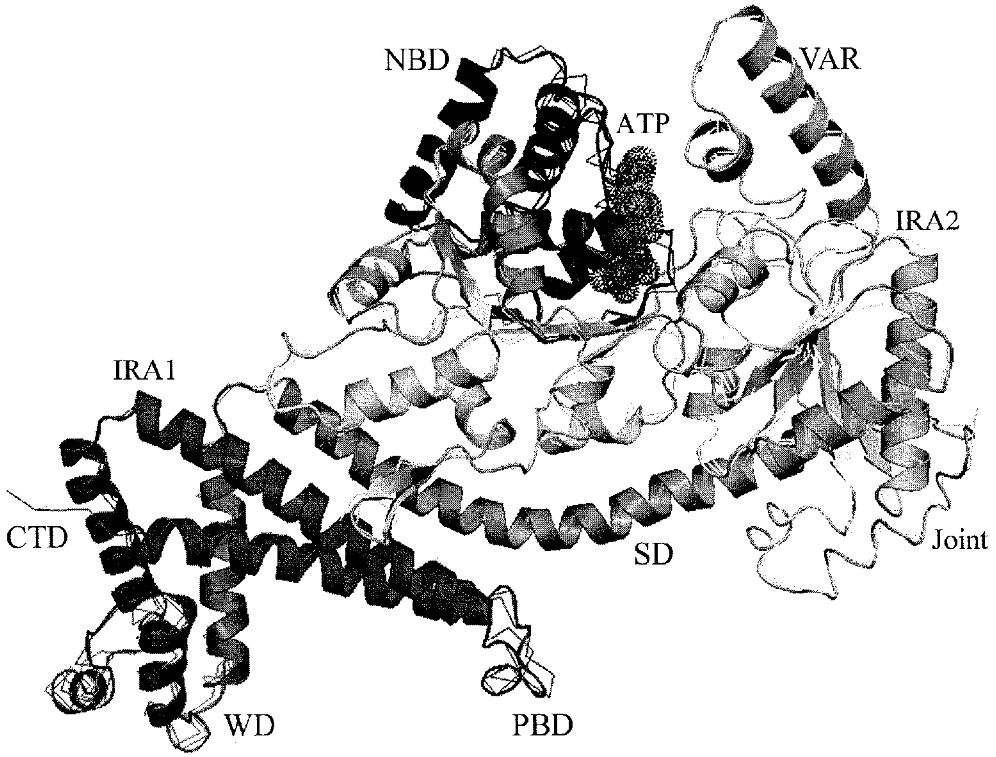
FIGS. 1A-1B illustrate a homology model of *Ca. L. asiaticus* SecA used for structure based design. (1A) Superimposed three-dimensional monomeric structures of SecA ATPase of *Ca. L. asiaticus* and *Escherichia coli* SecA (2FSG.pdb). The RMS deviation between these two proteins is 0.8 Å. Various domains of the protein structure were represented in different colors and defined as: NBD (Nucleotide Binding Domain), IRA (1 or 2) Intramolecular Regulator of ATPase, VAR (Variable region of IRA 2), CTD (Carboxy-Terminal Domain also called C-domain), SD (scaffold sub-domain) and WD (wing sub-domain). ATP binding site is in between NDB and IRA2-VAR domains in blue and green colors. (1B) Intermolecular interactions of ligand-protein (ATP—SecA of Las) complex after molecular minimization. H-bond interactions are observed between ATP and SecA active site residues including R344, G79, K82, T83, L84, Q61 & R56 and π-π interactions with F58 are also present. ATP is represented as stick model with dot surface and the remaining active site residues are in sticks.

The invention provides SecA inhibiting compounds that have antimicrobial activities. The term "inhibiting" indicatesa reduction in the rate or amount of a measurable interaction.

An SecA inhibiting compound of the present invention inhibits SecA activity in a Sec system, preferably in a bacterial Sec system, as measured by a block or delay in the ATP-hydrolysis process in a Sec system.

The SecA inhibiting compounds of this invention can be used in treating bacterial diseases of annual as well as perennial crops and ornamental plants. Preferably, the SecA inhibiting compounds are used with citrus plants; however, in other embodiments, the compounds of the invention can be used with a variety of plant species including, for example, trees, vines, forage, and annual plants.

The SecA inhibiting compounds of the invention are active against a variety of bacteria, including *Ca. L. asiaticus*. According to the subject invention, the SecA inhibiting compound interferes with the ATP binding pocket of SecA, thus affecting pre-protein translocation, including potential signal peptide dependent virulence factors of *Ca. L. asiaticus* and other bacteria.

Examples of SecA inhibiting compounds of the invention are as follows:

| Structure | ID | Mol Weight | Mol Formula | Mol Name | cLogP | LogSW | hDon | hAcc |
|---|---|---|---|---|---|---|---|---|
| 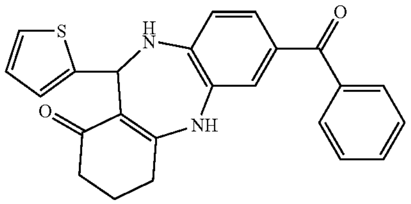 [SMILES: O=C1CCCC2=C1C(c1cccs1)Nc1ccc(C(=O)c3ccccc3)cc1N2] | C20 | 400.5 | $C_{24}H_{20}N_2O_2S$ | 7-benzoyl-11-(2-thienyl)-2,3,4,5,10,11-hexahydro-1H-diabenzo[b,e][1,4]diazepin-1-one | 3.95 | −5.493 | 2 | 2 |
| 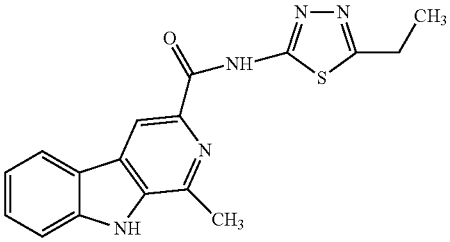 [SMILES: CCc1nnc(NC(=O)c2cc3c([nH]c4ccccc43)c(C)n2)s1] | C16 | 337.4 | $C_{17}H_{15}N_5OS$ | N-(5-ethyl-1,3,4-thiadiazol-2-yl)-1-methyl-9H-beta-carboline-3-carboxamide | 3.47 | −5.734 | 2 | 4 |
| 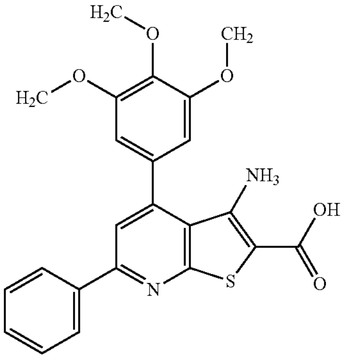 [SMILES: COc1cc(-c2cc(-c3ccccc3)nc3sc(C(=O)O)c(N)c23)cc(OC)c1OC] | C17 | 436.5 | $C_{23}H_{20}N_2O_5S$ | 3-amino-6-phenyl-4-(3,4,5-trimethoxy-phenyl)thieno[2,3-b]pyridine-2-carboxylic acid | 5.03 | −6.677 | 2 | 6 |
| 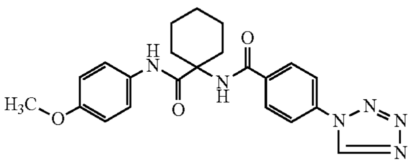 [SMILES: COc1ccc(NC(=O)C2(NC(=O)c3ccc(-n4cnnn4)cc3)CCCCC2)cc1] | C18 | 420.5 | $C_{22}H_{24}N_6O_3$ | N-(1-{[(4-methoxy-phenyl)amino]carbonyl}cyclo-hexyl)-4-(1H-tetrazol-1-yl)benzamide | 3.494 | −5.294 | 2 | 6 |
| 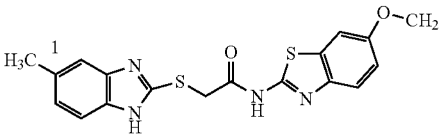 | C19 | 384.5 | $C_{18}H_{16}N_4O_2S_2$ | N-(6-methoxy-1,3-benzo-thiazol-2-yl)-2-[(5-methyl-1H-benz-imidazol-2-yl)thio]acetamide | 4.67 | −7.094 | 2 | 4 |

-continued
| Structure | ID | Mol Weight | Mol Formula | Mol Name | cLogP | LogSW | hDon | hAcc |
|---|---|---|---|---|---|---|---|---|
| 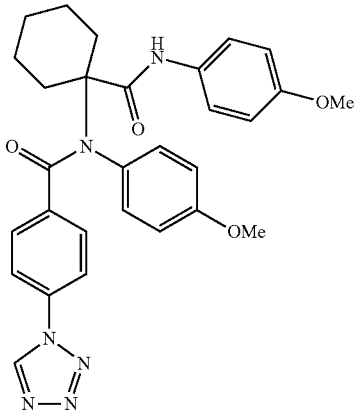 [SMILES: COc1ccc(NC(=O)C2(N(C(=O)c3ccc(-n4cnnn4)cc3)c3ccc(OC)cc3)CCCCC2)cc1] | SSC8 | 526.6 | $C_{29}H_{30}N_6O_4$ | N-(4-methoxy-phenyl)-N-{1-[(4-methoxy-phenyl) carbamoyl] cyclohexyl}-4-(1H-tetrazol-1-yl)benzamide | 4.62 | | 1 | 10 |
| 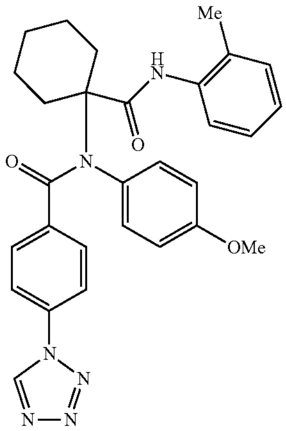 [SMILES: COc1ccc(N(C(=O)c2ccc(-n3cnnn3)cc2)C2(C(=O)Nc3ccccc3C)CCCCC2)cc1] | SSC11 | 510.6 | $C_{29}H_{30}N_6O_3$ | N-(4-methoxy-phenyl)-N-{1-[(2-methyl-phenyl) carbamoyl] cyclohexyl}-4-(1H-tetrazol-1-yl)benzamide | 4.97 | | 1 | 9 |
| 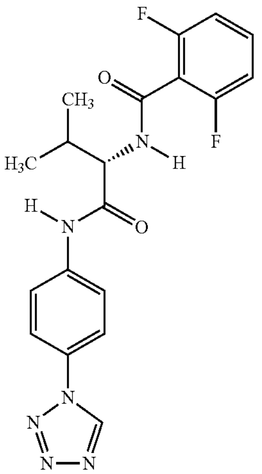 [SMILES: CC(C)[C@H](NC(=O)c1c(F)cccc1F)C(=O)Nc1ccc(-n2cnnn2)cc1] | SA1 | 400.1 | $C_{19}H_{18}F_2N_6O_2$ | 2,6-Difluoro-N-[(2S)-3-methyl-1-oxo-1-{[4-(1H-tetrazol-1-yl)phenyl] amino}-2-butanyl] benzamide | 1.93 | | 2 | 8 |

-continued
| Structure | ID | Mol Weight | Mol Formula | Mol Name | cLogP | LogSW | hDon | hAcc |
|---|---|---|---|---|---|---|---|---|
| 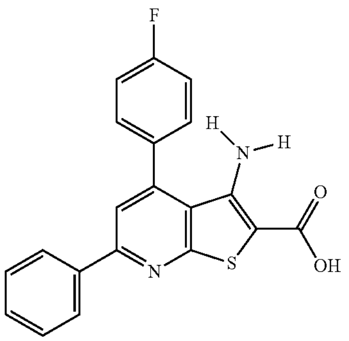 [SMILES: Nc1c(C(=O)O)sc2nc(-c3ccccc3)cc(-c3ccc(F)cc3)c12] | SA2 | 364.4 | $C_{20}H_{13}FN_2O_2S$ | 3-Amino-4-(4-fluorophenyl)-6-phenyl-thieno[2,3-b]pyridine-2-carboxylic acid | 5.01 | | 2 | 4 |
| 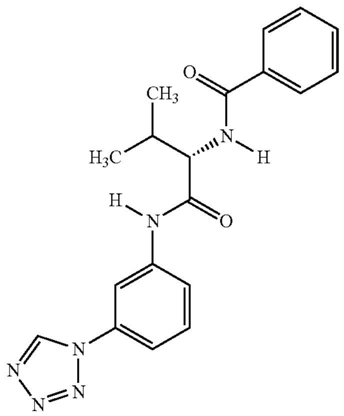 [SMILES: CC(C)[C@H](NC(=O)c1ccccc1)C(=O)Nc1cccc(-n2cnnn2)c1] | SA3 | 364.4 | $C_{19}H_{20}N_6O_2$ | N-[(2S)-3-Methyl-1-oxo-1-{[3-(1H-tetrazol-1-yl)phenyl] amino}-2-butanyl] benzamide | 1.89 | | 2 | 8 |
| 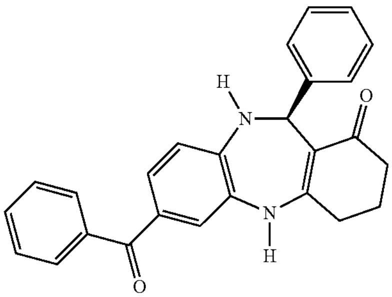 [SMILES: O=C1CCCC2=C1[C@H](c1ccccc1)Nc1ccc(C(=O)c3ccccc3)cc1N2] | SA4 | 394.5 | $C_{26}H_{22}N_2O_2$ | (11S)-7-Benzoyl-11-phenyl-2,3,4,5,10,11-hexahydro-1H-dibenzo[b,e] [1,4]diazepin-1-one | 5.12 | | 2 | 4 |
| 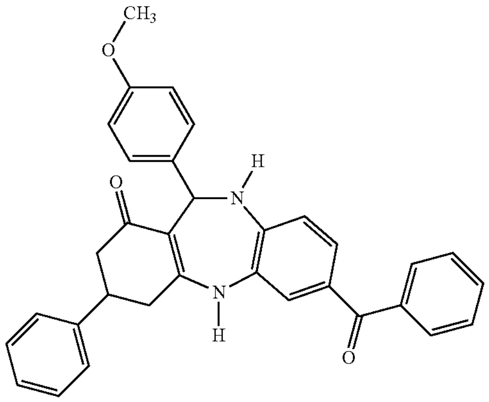 [SMILES: COc1ccc(C2Nc3ccc(C(=O)c4ccccc4)cc3NC3=C2C(=O)CC(c2ccccc2)C3)cc1] | SA5 | 500.6 | $C_{33}H_{28}N_2O_3$ | 7-Benzoyl-11-(4-methoxy-phenyl)-3-phenyl-2,3,4,5,10,11-hexahydro-1H-dibenzo[b,e] [1,4]diazepin-1-one | 6.74 | | 2 | 5 |

-continued

| Structure | ID | Mol Weight | Mol Formula | Mol Name | cLogP | LogSW | hDon | hAcc |
|---|---|---|---|---|---|---|---|---|
| 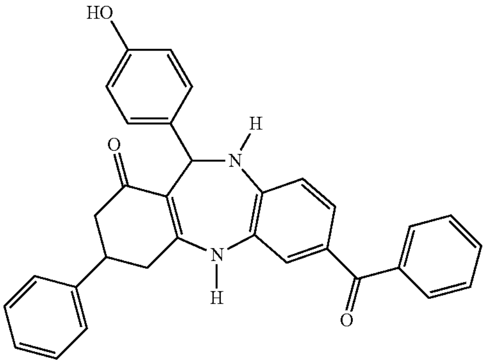 [SMILES: O=C1CC(c2ccccc2)CC2=C1C(c1ccc(O)cc1)Nc1ccc(C(=O)c3ccccc3)cc1N2] | SA6 | 486.6 | $C_{32}H_{26}N_2O_3$ | 7-Benzoyl-11-(4-hydroxy-phenyl)-3-phenyl-2,3,4,5,10,11-hexahydro-1H-dibenzo[b,e][1,4]diazepin-1-one | 6.21 | | 3 | 5 |
| 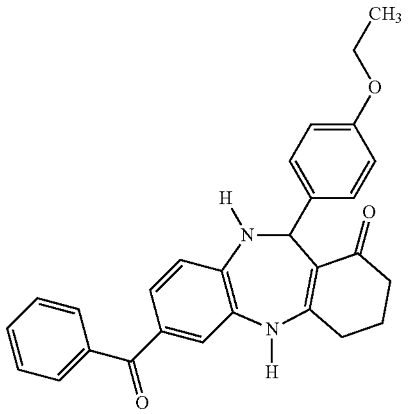 [SMILES: CCOc1ccc(C2Nc3ccc(C(=O)c4ccccc4)cc3NC3=C2C(=O)CCC3)cc1] | SA7 | 438.5 | $C_{28}H_{26}N_2O_3$ | 7-Benzoyl-11-(4-ethoxy-phenyl)-2,3,4,5,10,11-hexahydro-1H-dibenzo[b,e][1,4]diazepin-1-one | 5.55 | | 2 | 5 |
| 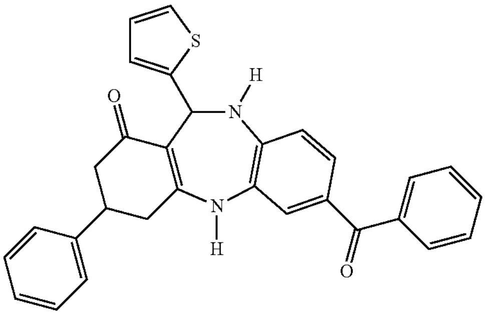 [SMILES: O=C1CC(c2ccccc2)CC2=C1C(c1cccs1)Nc1ccc(C(=O)c3ccccc3)cc1N2] | SA8 | 476.6 | $C_{30}H_{24}N_2O_2S$ | 7-Benzoyl-3-phenyl-11-(2-thienyl)-2,3,4,5,10,11-hexahydro-1H-dibenzo[b,e][1,4]diazepin-1-one | 6.58 | | 2 | 4 |
| 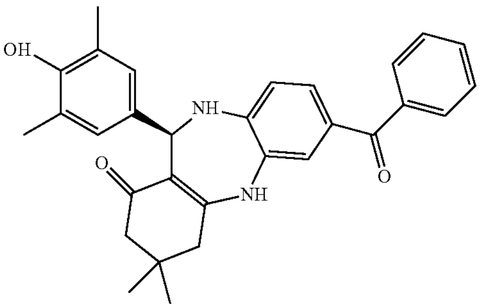 [SMILES: Cc1cc([C@H]2Nc3ccc(C(=O)c4ccccc4)cc3NC3=C2C(=O)CC(C)(C)C3)cc(C)c1O] | SA9 | 466.5 | $C_{30}H_{30}N_2O_3$ | 11-(4-hydroxy-3,5-dimethyl-phenyl)-3,3-dimethyl-7-(phenyl-carbonyl)-2,3,4,5,10,11-hexahydro-1H-dibenzo[b,e][1,4]diazepin-1-one | 6.31 | | 3 | 5 |

Their potent antimicrobial action is evident from their antimicrobial activities against *Agrobacterium tumefaciens* with MBC ranging from 128 μg/ml to 256 μg/ml.

In view of the aforementioned antimicrobial activities, the subject invention provides compositions comprising SecA inhibiting compounds, and salts thereof, as the active ingredient in anti-microbial compositions. The subject invention further provides methods of combating microbial growth through the use of an effective amount of the SecA inhibiting compounds, or salts thereof.

The subject compounds can be used in suitable solvents or diluents, in the form of emulsions, suspensions, dispersions, on suitable solid or semi-solid carrier substances, if desired, together with other compounds having antimicrobial activity.

Solid carrier substances that are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetable origin that are also suitable carrier substances.

The active ingredient is mixed with these carrier substances by, for example, being ground therewith. Alternatively, the inert carrier substance can be impregnated with a solution of an SecA inhibiting compound of the invention in a volatile solvent and the solvent is thereafter eliminated by heating or by filtering with suction at reduced pressure. By adding wetting and/or dispersing agents, such pulverous preparations can also be made readily wettable with water, so that suspensions are obtained.

Inert solvents used for the production of liquid preparations should preferably not be flammable and should be as far as possible odorless and as far as possible non-toxic to warm-blooded animals or plants in the relevant surroundings. Solvents suitable for this purpose are high-boiling oils, for example, of vegetable origin, and lower-boiling solvents with a flash point of at least 30° C., such as, for example, polyethylene glycol isopropanol, dimethylsulfoxide, hydrogenated naphthalenes and alkylated naphthalenes. It is, of course, also possible to use mixtures of solvents. Solutions can be prepared in the usual way, if necessary, with assistance of solution promoters.

Other liquid forms that can be used include emulsions or suspensions of the active compound in water or suitable inert solvents, or also concentrates for preparing such emulsions, which can be directly adjusted to the required concentration. For this purpose, an SecA inhibiting compound of the invention can be, for example, mixed with a dispersing or emulsifying agent. The active component can also be dissolved or dispersed in a suitable inert solvent and mixed simultaneously or subsequently with a dispersing or emulsifying agent.

Furthermore, it is possible for the SecA inhibiting compounds of the invention to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria, e.g., in closed chambers and storage rooms, and for application to vegetation for eradicating or for preventing infections by bacteria.

The subject compounds and compositions thereof can be applied by conventional methods. For example, a plant to be treated or to be protected against attack by bacterium can be treated with the subject compounds and the compositions thereof by dusting, sprinkling, spraying, brushing, dipping, smearing, impregnating, injection into the vascular system, application to root system or other suitable means. In a preferred embodiment, the SecA inhibiting compounds of the invention are directly injected in the vascular system of a plant.

When the subject SecA inhibiting compounds are employed in combination with suitable carriers, e.g., in solution, suspension, dust, powder, ointment, emulsion, and the like forms, a high activity over a very high range of dilution is observed. For example, concentrations of the SecA inhibiting compounds can range from 100 μM, 500 μM and 1 mM. Of course, higher or lower concentrations may also be employed as warranted by the particular situation. Moreover, the subject SecA inhibiting compounds can be employed with other programs, such as commercial fertility programs.

Following are examples which illustrate procedures for practicing the invention. These examples should not be construed as limiting. All percentages are by weight and all solvent mixture proportions are by volume unless otherwise noted.

EXAMPLE 1

Activity of SecA Inhibiting Compounds

Materials and Methods

Computational Methodology

Homology model of SecA was built with Prime structure prediction of Schrodinger software (Schrödinger, LLC (2005) Schrödinger Suite 2006. Induced Fit Protocol, Prime version 1.5, Schrödinger, LLC, New York). Reported X-ray crystal structures in Protein Data Bank (PDB ID: 2VDA, 2FSF & 2FSG) (Papanikolau, Y., Papadovasilaki, M., Ravelli, R. B., McCarthy, A. A., Cusack, S., Economou, A., Petratos, K. (2007). Structure of dimeric SecA, the *Escherichia coli* preprotein translocase motor. J. Mol. Biol. 366, 1545-1557; and Gelis, I., Bonvin, M. A., Keramisanou, D., Koukaki, M., Gouridis, G., Karamanou, S., Economou, A., Kalodimos, C. G. (2007). Structural Basis for Signal-Sequence Recognition by the Translocase Motor SecA as Determined by NMR. Cell. 131, 756-769) of *E. coli* SecA homodimer bound with ATP was used to build SecA homology model of Las. The coordinates for all reported proteins were obtained from the PDB.

Structures were prepared using the Maestro (Schrödinger, LLC (2005). Maestro, Version 7.5, Schrödinger, LLC, New York) software package and aligned using the Protein Structure Alignment module in Prime. If a PDB structure was missing side-chain atoms, Prime was used to predict their locations. Water molecules in all structures were removed. A brief relaxation was performed on each starting structure using the Protein Preparation module in Maestro with the "Refinement Only" option. The modeled protein structure was prepared with appropriate bond orders and formal charges by protein preparation wizard of Maestro module. Then ATP ligand was manually docked as reported (Akula, N., Zheng, H., Han, F. Q., Wang, N. (2011). Discovery of novel SecA inhibitors of *Candidatus Liberibacter asiaticus* by structure based design. Bioorg. Med. Chem. Lett. 15, 4183-4188) against the homology model and ligand-protein complexes were energy minimized. The receptor grid file was generated by excluding ATP and defining 8 Å radius from ATP without any constraints.

Structure-based virtual screening was used to screen putative SecA inhibitors from approximately 11 million small molecule compounds available from ZINC[11] database (Irwin and Shoichet, (2005). ZINC—A Free Database of Commercially Available Compounds for Virtual Screening. J. Chem. Inf. Model. 45, 177-182). To reduce the workload into the pipeline, twenty thousand structures were selected based on the physicochemical properties e.g. Net charge (−1 to +1), H-Bond donor/acceptor (2-6), and molecular weight (300-600 Da). Glide program (Friesner, R. A., Banks, J. L., Murphy, R. B., Halgren, T. A., Klicic, J. J., Mainz, D. T., Repasky, M. P., Knoll, E. H., Shelley, M., Perry, J. K., Shaw, D. E., Francis, P., Shenkin, P. (2004). Glide: A New Approach for Rapid, Accurate Docking and Scoring. 1. Method and Assessment of Docking Accuracy. J. Med. Chem. 47, 1739-1749) was used to build receptor grid file and for the docking studies.

Molecular minimization of ATP, highly active ligands with protein complexes were performed by Macromodel suite program (Mohamadi, F., Richards, N. G. J., Guida, W. C., Liskamp, R., and Lipton, M. (1990). MacroModel—an Integrated Software System for Modeling Organic and Bioorganic Molecules Using Molecular Mechanics. J. Comput. Chem. 11, 440-467). OPLS (Jorgensen, W. L., Maxwell, D. S., and Tirado-Rives, J. (1996). Development and Testing of the OPLS All-Atom Force Field on Conformational Energetics and Properties of Organic Liquids. J. Am. Chem. Soc. 118, 11225-11236) force field and "distance-dependent" dielectric constant were used during minimization. All the minimizations were carried out by means of 5000 iterations of Polak-Ribiere conjugate gradient method and followed by converge on gradient until a convergence threshold of 0.05 kJ/mol.Å. All the molecular modeling studies have been performed on HP ProLiant, RedHat Linux operating system and docking postures were taken by PYMOL program (DeLano, L. L. (2002).

Inhibition Assay Against SecA of Las

Cloning, expression, and purification of SecA were conducted as described previously (Akula, N., Zheng, H., Han, F. Q., Wang, N. (2011). Discovery of novel SecA inhibitors of *Candidatus Liberibacter asiaticus* by structure based design. Bioorg. Med. Chem. Lett. 15, 4183-4188). Quantichrom ATPase/GTPase kit (Bioassay Systems, Hayward, Calif.) was used to test the inhibitory effect of different compounds on SecA of *Ca. L. asiaticus* as described previously (Denis, L., Guy, G. P., and Andrien, R. B. (1978). A convenient method for the ATPase assay. Anal. Biochem. 85, 86-89; and Richard, D. H., John, L. V., and Richard, A. W. (1998). A microassay for ATPase. Anal. Biochem. 169, 312-318). All these assays were done in triplicate and repeated three times with similar results. The OD values are measured from Benchmark plus ELISA micro plate spectrophotometer (Bio-Rad Hercules, Calif.). ATPase activities were determined by the release of phosphate ion (Pi) detected spectrophotometrically, using malachite green and inhibition was calculated by showing the percentage (%) of the remaining ATPase activities (Akula ibid.).

Antimicrobial Activity Against *A. tumefaciens*

*A. tumefaciens* was obtained from the culture collection of citrus associated bacteria initially isolated from the roots and rhizosphere of citrus and maintained in our laboratory as glycerol stock stored at −80° C. Minimum bactericidal concentrations (MBC) of the selected compounds against *A. tumefaciens* were determined by the broth microdilution method. Streptomycin was used as a positive control. Each small molecule compound was dissolved in DMSO and two-fold serially diluted with LB medium to give final concentrations of 8 μg/ml to 512 μg/ml. Aliquots of 100 μl were poured into 96-well microplates. *A. tumefaciens* was grown overnight and diluted with LB medium to give final concentrations $5\times10^5$ colony-forming unit (CFU) $ml^{-1}$. Samples of 100 μl were inoculated onto LB microdilution plates containing the tested compounds and incubated at 28° C. for 24 h. After 24 h of incubation at 28° C., 100 μl samples from different dilutions were transferred onto antibiotic-free LB agar plates, which were then incubated at 28° C. After incubation for 2 days, the number of colonies recovered was counted. Survival rate was determined as the percentage of recovered cells compared to viable cells in the initial inoculum. MBC was defined as the lowest drug concentration producing a survival rate of <0.1%. Experiments were carried out in triplicate and repeated three times.

Results and Discussion

Homology Modeling & Optimization of ATP Binding Site

Figure 1B:
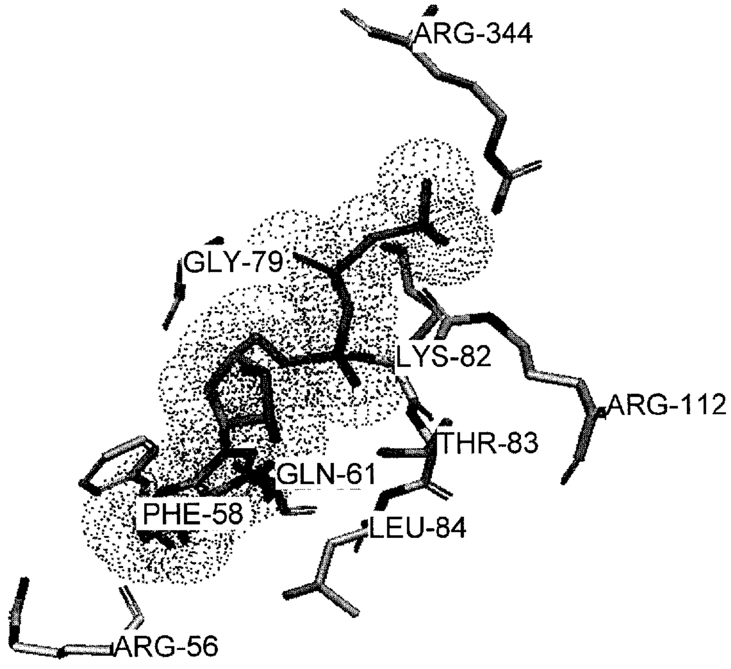

Previously, only one PDB structure (2FSG) was used as a template to build the SecA homology model (Akula, N., Zheng, H., Han, F. Q., Wang, N. (2011). Discovery of novel SecA inhibitors of *Candidatus Liberibacter asiaticus* by structure based design. Bioorg. Med. Chem. Lett. 15, 4183-4188). In this study, three PDB structures (2VDA, 2FSF and 2FSG) were used as templates to further optimize the homology model of SecA. The precise positions, orientations/conformations of the helices in the homology modeled SecA are slightly different from the reported templates. The homology model of SecA was used to superimpose on the reported PDB (2FSG) structure to identify the ATP binding site on SecA protein of *Ca. L. asiaticus* (FIGS. 1A-1B). The ATP-binding site is located in between NBD and IRA2-VAR. ATP was extracted from 2FSG and was manually placed on SecA at the similar receptor site of the model and merged with the ligand protein complex (FIG. 1A). Then the ligand protein complex was minimized using OPLS5 force field with 5000 minimization cycles until the minimization was terminated once the RMSD reached a maximum value of 0.05 Å. The intermolecular interactions were also observed. In the optimized complex, ATP retained its orientation without losing the H-bond interactions between ATP and SecA active site residues (R344, G79, K82, T83, L84, Q61 and R56). The observed π-π interactions with F58 were similar to the reported crystal structure (FIG. 1B).

Molecular Docking: High Throughput Virtual Screening/SP/XP

Figure 2:
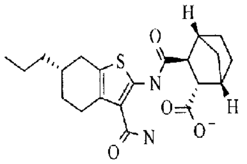
FIG. 2 provides the structures of 20 inhibitory compounds (C1-C20) against SecA of Las.
Figure 2:
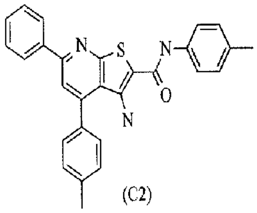
Figure 2:
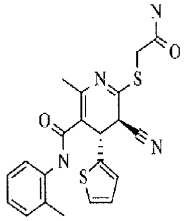
Figure 2:
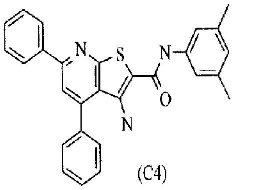
Figure 2:
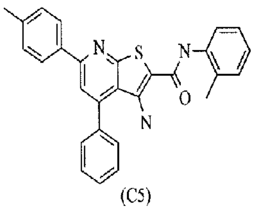
Figure 2:
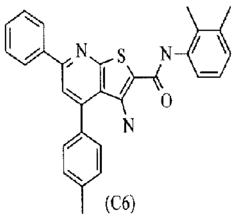
Figure 2:
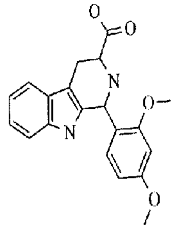
Figure 2:
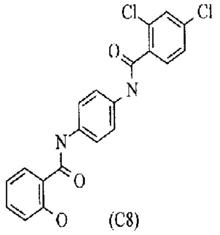
Figure 2:
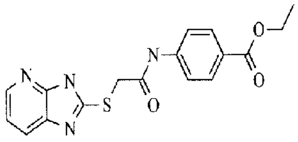
Figure 2:
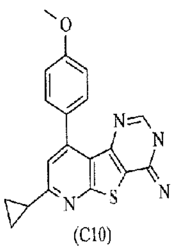
Figure 2:
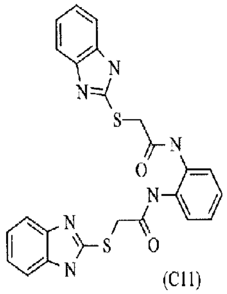
Figure 2:
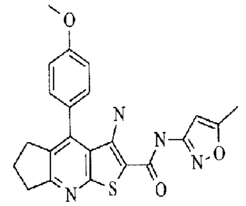
Figure 2:
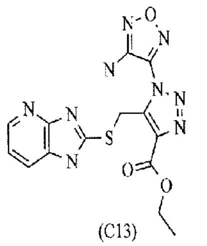
Figure 2:
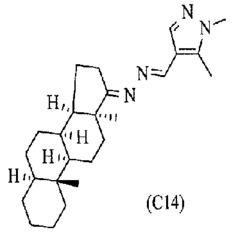
Figure 2:
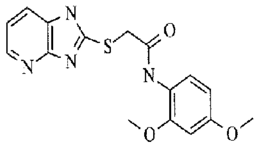
Figure 2:
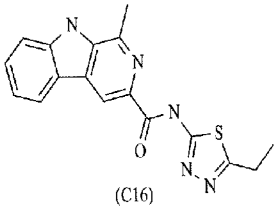
Figure 2:
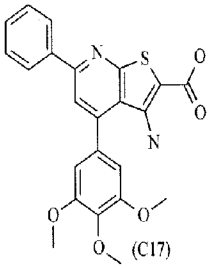
Figure 2:
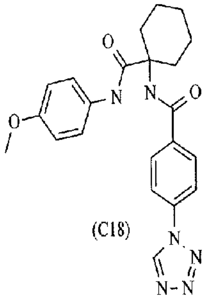
Figure 2:
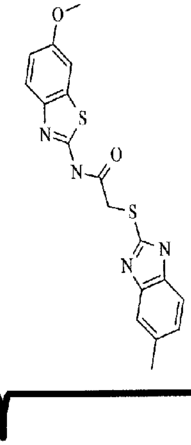
Figure 2:
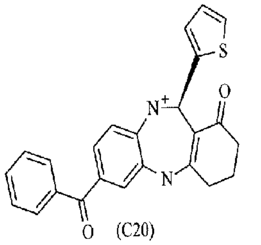

High throughput screening (HTVS) by molecular docking was performed and calculated docking scores to filter the structures, and the filtrates were subjected to standard and extra precision docking to evaluate the scoring functions. Approximately, 20,000 structures identified from the physicochemical properties were subjected to glide HTVS to filter the low scoring ones. The initial step to screen the small molecule databases is grid generation. Receptor grid file was generated that enabled Glide (Friesner, R. A., Banks, J. L., Murphy, R. B., Halgren, T. A., Klicic, J. J., Mainz, D. T., Repasky, M. P., Knoll, E. H., Shelley, M., Perry, J. K., Shaw, D. E., Francis, P., Shenkin, P. (2004). Glide: A New Approach for Rapid, Accurate Docking and Scoring. 1. Method and Assessment of Docking Accuracy. J. Med. Chem. 47, 1739-1749) to search for favorable interactions between the ligand and ATP binding-site region. The shape and properties of the receptor are represented on a set of grids for positioning and scoring ligand poses. From HTVS, approximately 5000 structures were selected based on the docking scores against SecA. The resulting poses of the docked compounds were ranked according to their Glide standard and extra precision docking scores. Compounds detected by 2D and 3D ligand-based searches were analyzed with the binding modes, intermolecular interactions, and with the chemical intuition twenty compounds selected for biological activity studies (FIG. 2).

Inhibitory Assay Against SecA ATPase Activity of *Ca. L. asiaticus* and Antimicrobial Assay Against *A. tumefaciens*

Figure 3A:
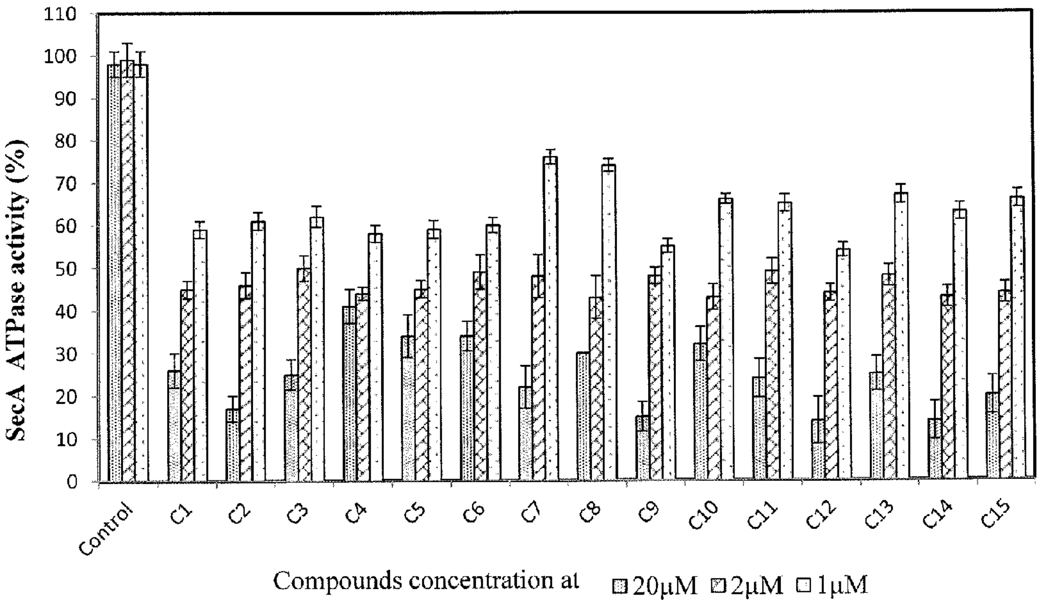
FIGS. 3A-3B show inhibitory activities of C1-C20 compounds against SecA of *Ca. L. asiaticus*. (3A) Compounds 1-15 at 20 μM, 2 μM & 1 μM concentrations; (3B) Compounds C16-C20 at 1 μM, 750 nM, 500 nM, 250 nM, 200 nM, 100 nM & 50 nM concentrations.
Figure 3B:
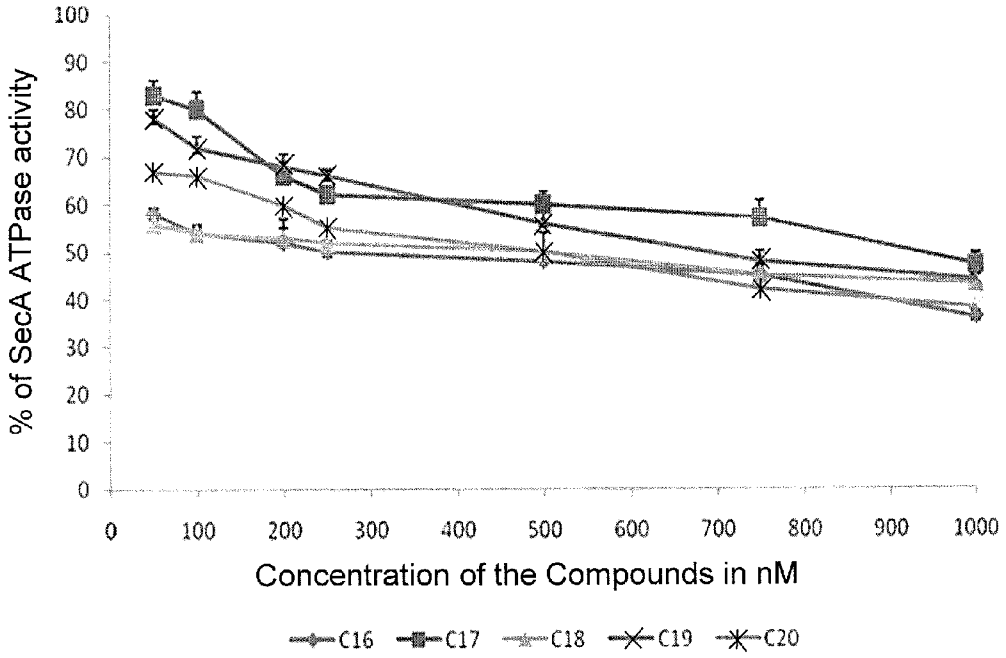

The selected twenty compounds were tested for their inhibition against SecA ATPase activity. Among the twenty compounds, only five of them showed greater than 50% inhibition at 1 μM (FIG. 3A). The $IC_{50}$ values of the five compounds C16, C17, C18, C19, and C20 were 0.25, 0.92, 0.48, 0.64, and 0.44 μM respectively. These values are calculated based on the 50% remaining ATPase activity (FIG. 3B).

The minimal bactericidal concentrations (MBCs) of the five identified compounds and streptomycin were determined by broth microdilution method. The MBC values of five compounds C16, C17, C18, C19, C20 and streptomycin are 256, 256, 256, 128, 256 and 64 μg/ml, respectively. The MBC values of all compounds are 2-4 fold higher than streptomycin.

Figure 4A:
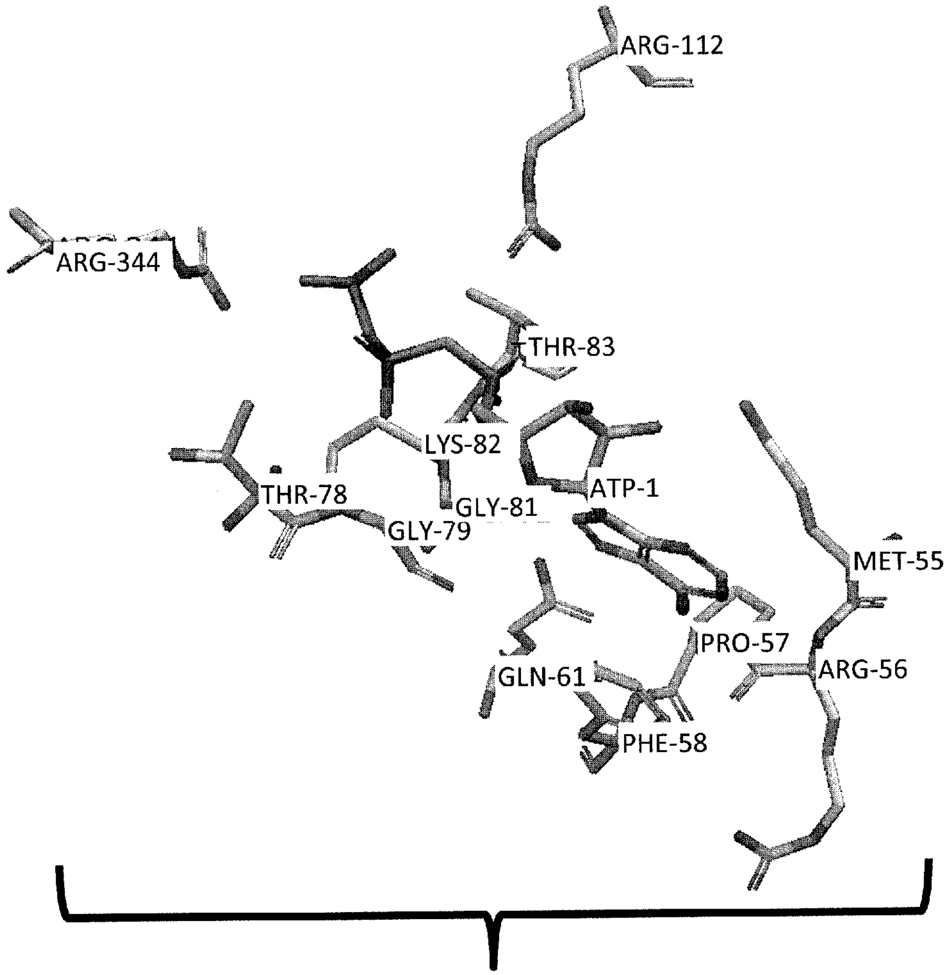
FIGS. 4A-4C illustrate the molecular docking interactions of SecA with different ligands including ATP, high & low activity structures. Intermolecular H-Bond interactions, between ligand-protein complexes. (4A) ATP-SecA active site interactions with R344, R112, T78, T83, Q64 & P57 (Dock Score: −8.7412 k.cal/mol); (4B) C16-SecA active site interactions with R344, T83, K82 & Q64 (Docking Score: −7.2140 k.cal/mol); (4C) C4-SecA active site interactions with T83 & Q64 (Docking Score: −5.6561 k.cal/mol).
Figure 4B:
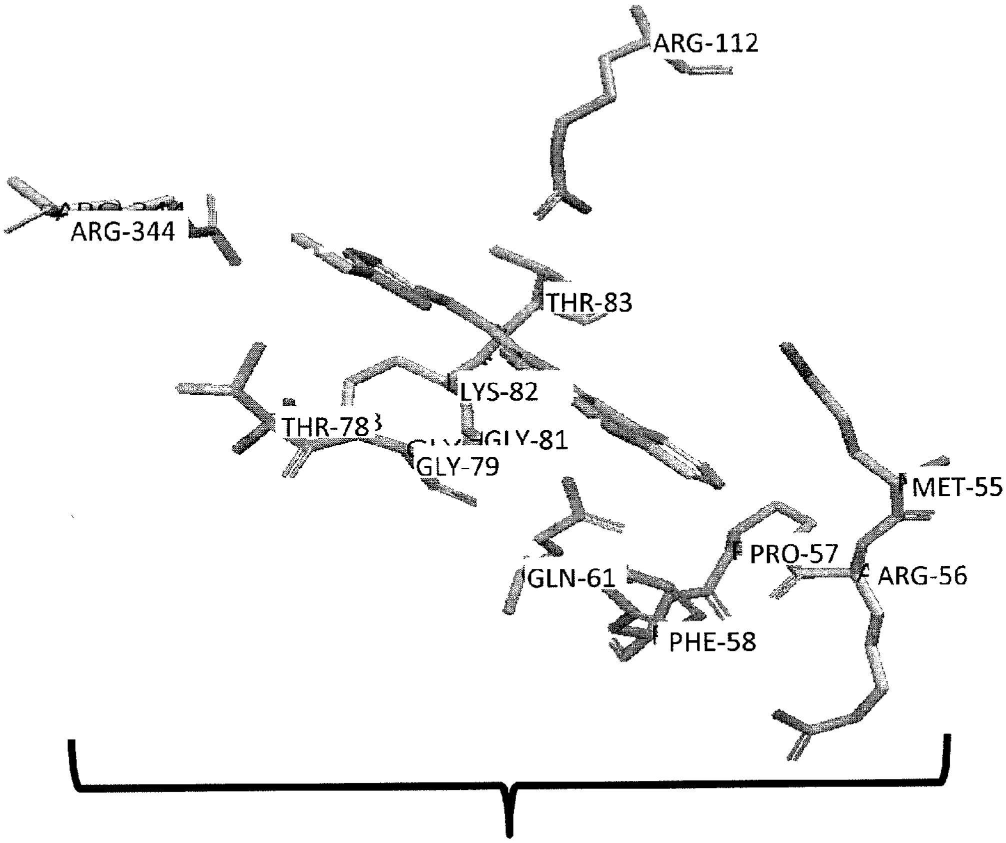
Figure 4C:
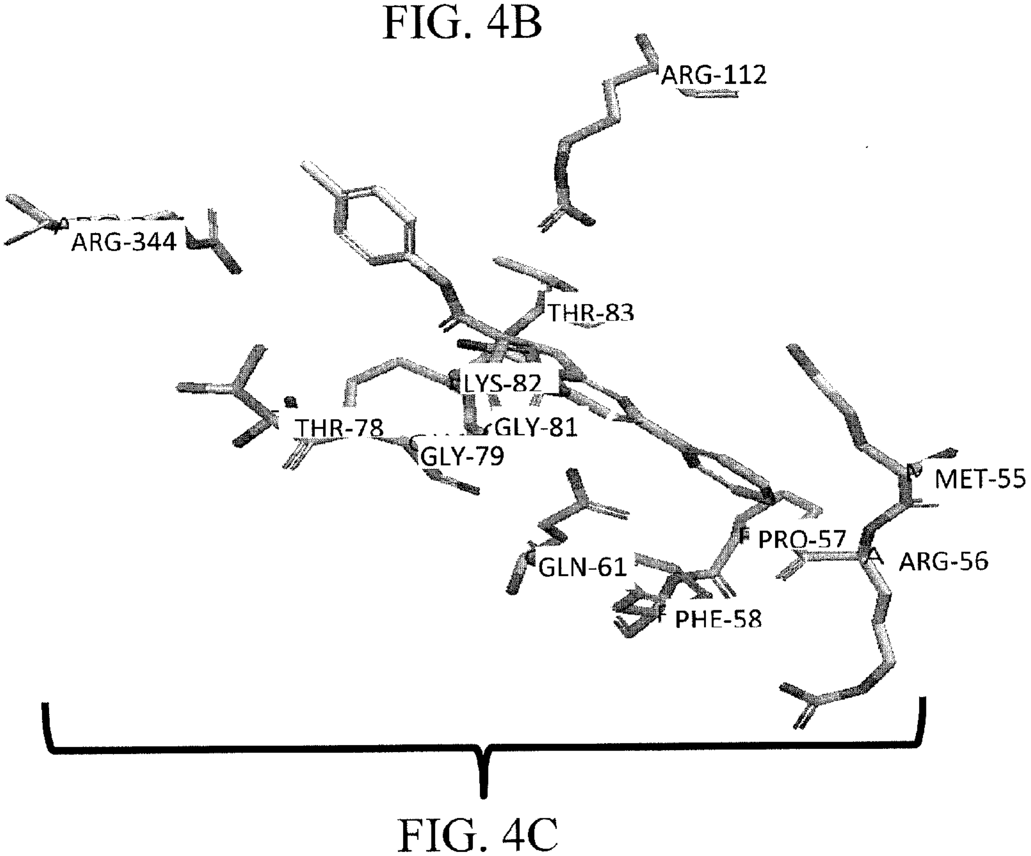

Molecular Docking and Minimization: Comparative Study of ATP Binding of High and Low Activity Compounds The optimized homology model of SecA was used for molecular docking study. To validate the generated grid model and molecular docking methodology, the ATP structure was docked to the active site of SecA of Las. Glide Xtra-Precision software was used to rigidly dock the ligand at the binding site of the *Ca. L. asiaticus* SecA without any constraints and water molecules. The obtained results indicate that the binding mode of ATP inside the receptor is similar and in agreement with the experimental mode of the crystal structure (FIG. 4A). This result indicates that the receptor grid file can be used to dock rigidly with the selected twenty structures. The observed dock results of the identified twenty structures showed similar binding orientations and π-π interactions with Phe58 as ATP. The structural difference and binding mode between high & low activity structures were analyzed and compared with ATP in order to understand the differences between the activities among the compounds. Specifically ATP is involved in several H-Bond interactions in the active site due to presence of more nucleophilic phosphate groups. Also the adenine moiety has π-π stacking with the aromatic ring of residues Phe58 and forms H-Bond with Gln64 (FIG. 4A). The conformational orientation of rigidly docked ATP at *Ca. L. asiaticus* SecA binding sites is slightly different from its original minimized ATP-SecA complex. Nevertheless, the critical interactions with Arg344, Arg112, Thr83, Gly79 and Phe58 remained the same in both models (FIGS. 1B & 4A). The high activity structure C16 displayed similar interactions as ATP, particularly in H-Bond interactions (involving residues Gln64, Lys82, Thr83 & Arg344) and π-π stacking with Phe58 (FIG. 4B). The low activity structure C4 lacked of interactions with the inside binding site residues Gly81, Lys83 & Arg344 which are more important to keep the ligand inside the binding site to competitively inhibit the ATP. Although the low activity structure has π-π stacking with its aromatic ring and Phe58 (FIG. 4C), the lack of internal interactions might be responsible for the lower activity of C4 compound. In addition, the docking scores also correlated well with the in vitro activities of C16 & C4. These experimental and theoretical results indicated the importance to study residue interactions for selecting compounds with higher activity against selected proteins.

Figure 5A:
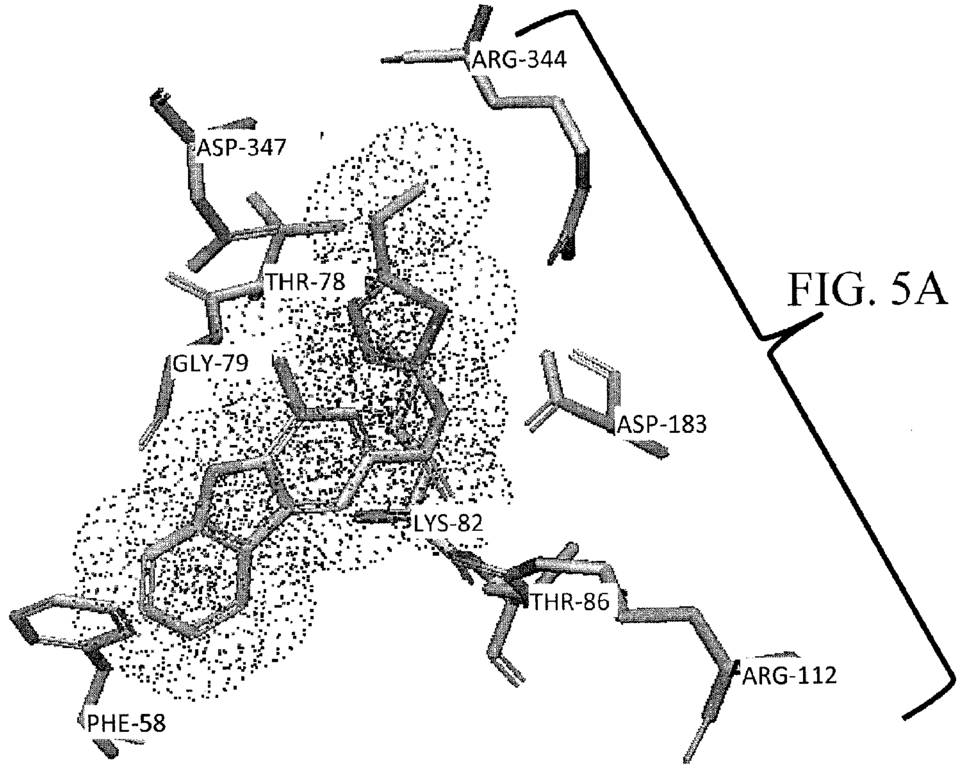
FIGS. 5A-5B illustrate the intermolecular interactions of SecA with ligand after molecular minimization. Intermolecular (H-bond, Hydrophobic & π-π) interactions between ligand-Protein complexes. (5A) C16-SecA active site interactions with R344, D347, T78, G79, K82, T83, R112 & F58 (Binding Energy: −73878 k.cal/mol); (5B) C4-SecA active site interactions with D347, T83, L84 & F58 (Binding Energy: −73039 k.cal/mol).
Figure 5B:
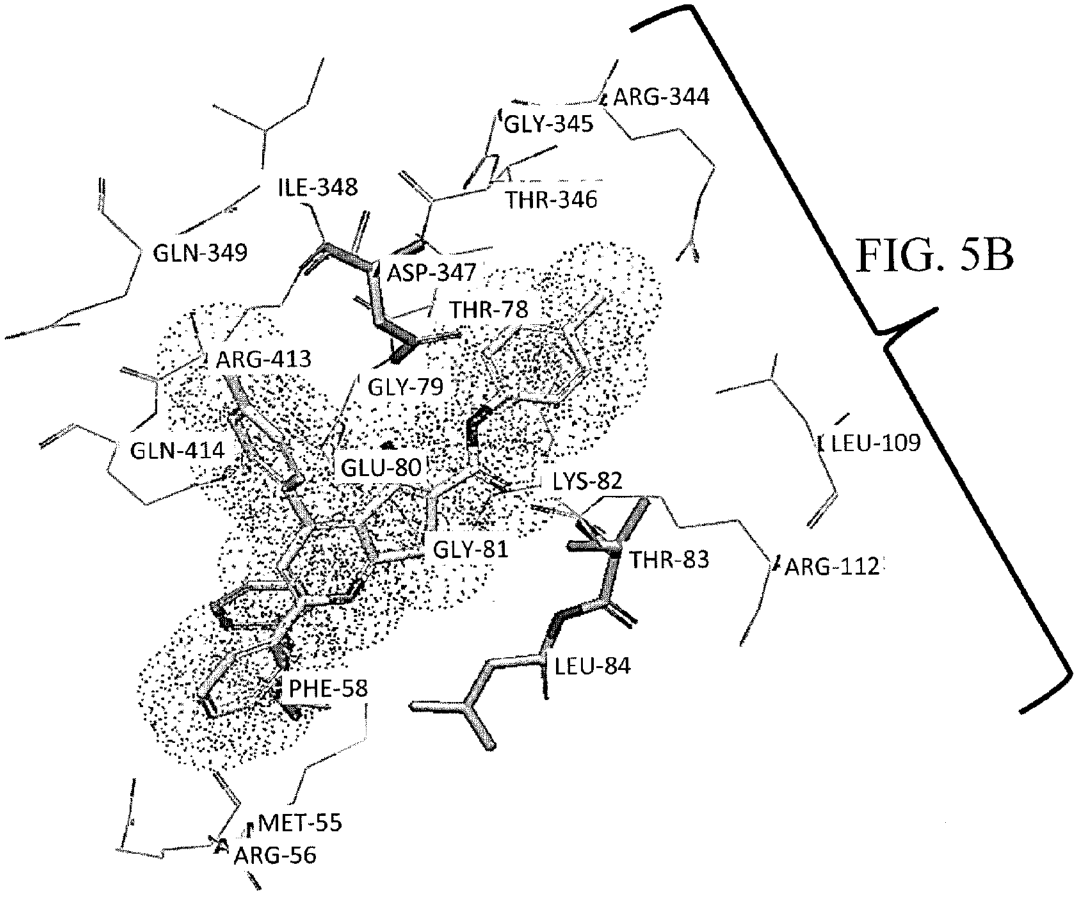

To further understand the difference between high and low activity structures, energy minimization studies were performed after the molecular docking analysis. While the docking methodology facilitates studying the binding of the *Ca. L. asiaticus* SecA inhibitors with flexible and rigid biding modes, it does not allow the protein mobility. In order to give free molecular motion of SecA protein along with ligands, the ligand protein complexes were minimized and the binding energies calculated (FIGS. 5A-5B). Interestingly, it was observed that the high activity structure C16 has hydrophobic interactions with active site residues (Thr78, Gly79 & Arg344) along with other contacts after energy minimization, whereas the low activity structure C4 is missing many of these interactions in energy minimized complex. This demonstrates that the electronic effects of these substituents have an impact toward higher affinity. The need for a strong H-bond donor/acceptor in the ligand is critical for the binding interactions between the ligand and active site residues. The lack of these interactions in low activity compounds results in minor competitive inhibition of ATP binding compared with high activity compounds.

Conclusions

Structure based virtual screening was performed to identify the novel SecA inhibitors of Las. Five compounds were found to inhibit the ATPase activity of SecA of *Ca. L. asiaticus* in nano molar concentrations. These compounds showed antimicrobial activities against *A. tumefaciens* with MBC ranging from 128 μg/ml to 256 μg/ml. Molecular docking and minimizations studies showed the correlation between the experimental and theoretical studies.

EXAMPLE 2

Effect of Compound C16 and Oxytetracycline on Reducing CLAS Populations

TABLE 1

One-way ANOVA analysis of effect of C16 and oxytetracycline on reducing CLAS populations

| Treatments | Before | 2 days after treatment | 4 days after treatment |
|---|---|---|---|
| Water | 23.35 a | 23.21 a | 22.64 a |
| C16 | 22.71 a | 23.76 a | 25.43 b |
| Oxytetracycline | 25.36 a | 26.10 b | 25.61 b |

Numbers with the same letter in a column indicates no significance at $P<0.05$; Numbers with the different letters in a column indicate significance at $P<0.05$. The number in each table cell is the mean Ct value for a sample (a quantitative PCR procedure to determine the CLAS populations); the statistical test used is Fisher's LSD method.

Conclusion:

There was significant effect ($P<0.05$) of CLAS population reduction in the treatments of both C16 and oxytetracycline as compared to water-treated control (Table 1).

EXAMPLE 3

Effect of C16 and Streptomycin on Reducing the CLAS Transmission Rate Using Graft-Based Approach Plant Materials HLB-infected budwoods were collected in HLB infected grove in teaching block at CREC. The presence of CLAS titers in budwood was confirmed by qPCR.

Treatments

C16 and streptomycin were applied at the rate of 500 μg/ml; water-treated budwood was used as check. The budwoods were placed in a glass bottle containing either treatment or water as check. The glass bottles were kept in a ventilation hood with light on to increase the evaporation rate, therefore, promoting the uptake of antibiotics. Leaf and bark samples were collected from each budwood and 100 mg were accurately weighed and used for DNA extraction with Promega genomic DNA extraction kit. CLAS populations in each sample were determined using standard qPCR protocol. Each DNA sample was run in triplicate wells.

After overnight treatment, the antibiotic-treated budwood was grafted onto 2-3 years old Valencia trees. A total of 15 trees were grafted for each treatment. Three and five months after grafting, all 45 trees were sampled to determine whether CLAS has been transmitted through antibiotic-treated scion. Four leaves from the main stem of Valencia trees were sampled for DNA extraction and determination of CLAS populations.

TABLE 2

Effect of C16 and streptomycin on reducing CLAS.

| Treatments | CLAS transmission rate (% trees tested positive for CLAS) 3 months after grafting | 6 months after grafting |
|---|---|---|
| Water | 26.7 | 100 |
| C16 | 6.7 | 80 |
| Streptomycin | 13.3 | 66.7 |

The number in each table cell is the mean Ct value for a sample (a quantitative PCR procedure to determine the CLAS populations); the statistical test used is Fisher's LSD method.

Conclusion

C16 and streptomycin has reduced the CLAS transmission rate by 20% to 35% as compared to water control, which had 100% transmission rate of CLAS (Table 2).

EXAMPLE 4

Activities of the Compounds of the Current Invention Against Various Bacteria Bacterial Strains and their Sub-Culturing Conditions Cultures of *Agrobacterium tumefaciens* and *Escherichia coli* strain DH5α were maintained in LB medium at 28° C. and 38° C., respectively; *Liberibacter crescens* and *Xanthomonas citri* subsp. *citri* was grown in BM7 medium (Leonard, 2012) and nutrient broth at 28° C. *Rhizobium etli* (ATCC 51251), *Bradyrhizobium japonicum* (ATCC 10324), *Mesorhizobium loti* (ATCC 700743), *Sinorhizobium meliloti* (RM1021) were grown in Yeast-Mannitol broth at 28° C. Bacterial culture was grown to the logarithmic-phase to match the turbidity of 0.5 McFarland standard (Andrew, 2001). Thereafter, the bacterial suspensions were adjusted to approximately $10^6$ CFU/mL with appropriate medium. A total of 100 μl of inoculum were added to a well in MIC plates.

Determination of Minimum Inhibitory Concentration (MIC)

The MIC is defined as the lowest concentration of a compound that inhibits visible growth of an organism after overnight incubation (this period of 20-24 h is extended for slowly growing organisms such as anaerobes that require longer incubation for growth) (Andrew, 2001; Wallace J R. et al, 1986). In our case, appropriate incubation period was chosen for each bacterial species according to their varying doubling time (Table 3). The broth microdilution method (Andrew, 2001; Jorgensen, 2009; Wallace J R. et al, 1986) was used to test a microorganism for its ability to produce visible growth. MIC plates were prepared with a 96-well microplate containing eight different levels of twofold dilution series of antimicrobial compounds. Antimicrobial compounds were dissolved in the formulation MM1 and twofold dilution series starting from 1024 μg/ml to 8 μg/ml were made in appropriate broth. A total of 100 μl were added to a well and each concentration was replicated in 4 wells. For each bacterial species, streptomycin and oxytetracycline was included as check. In addition, four wells containing only 200 μl broth and four wells containing broth and inoculum were also included to each MIC plate. A total of 23 antimicrobial compounds were subjected to test in this study. After incubating for appropriate period, MIC plates were examined for visible bacterial growth as evidenced by turbidity. Turbidity of MIC plates was also recorded in a microplate reader at a wavelength of 630 nm.

TABLE 3

Doubling time of bacterial species used in this study

| Bacterial species | Incubation period | Doubling time | References |
|---|---|---|---|
| *Escherichia coli* strain DH5α | 20 hr | 38-45 min | Lin, 2010 |
| *Agrobacterium tumefaciens* | 20 hr | 1 hr 45 min | Chilton, 1974 |
| *Xanthomonas citri* subsp. *citri* | 24 hr | 2 hr | Silva, 2013 |
| *Sinorhizobium meliloti* (RM1021) | 36 hr | 3 hr | Barloy-Hubler, 2004 |
| *Mesorhizobium loti* | 36 hr | 4 hr | Hanyu, 2009 |
| *Rhizobium etli* | 72 hr | 5 hr | Dombrecht, 2005 |
| *Bradyrhizobium japonicum* | 96 hr | 20 hr | Shah, 2006 |
| *Liberibacter crescens* | 120 hr | 36 hr | Fagen, 2014 |

Determination of Minimum Bactericidal Concentration (MBC)

MBC is defined as the lowest concentration of a compound with the reduction by 99.9% of the initial inoculum of multiplying bacteria within the incubation period. While the MBC test is not well established and less reproducible (Taylor, 1983), the majority of literature on MBC measurement followed the procedure as follows: after MIC reading, 100 μl of bacterial suspension samples was taken from the first well with turbidity and all clear wells and inoculated on a 9-cm agar plate containing appropriate medium without antimicrobial compound. The inoculated plates were incubated under conditions as described for MIC test. Plates with colony forming number less than 50 were considered as MBC. Alternatively, MBC was determined by centrifuging the MIC plate at 4000 rpm for 8 min, removing supernatant (containing antimicrobial compounds), adding 200 μl of appropriate broth and incubating under conditions as described for MIC test. After incubating the plate for appropriate period (Table 3), the plate was examined for visible bacterial growth as evidenced by turbidity; MBC is the lowest concentration in wells that stayed clear.

MIC and MBC tests of various compounds against the bacteria tested according to the claimed invention are provided in Tables 4-10. Concentration of the compounds is in μg/ml and the solvent contains N-methyl-2-pyrrolidone: Hallcomide M 8-10:Tergitol L-61:Rhodafac RS 610:Emulpon CO-360 in the ratio of 20:10:8.8:1.6:59.6.

TABLE 4

Inhibitory activity against *Liberibacter crescens*.

| Compound | 24 hrs MIC | 24 hrs MBC | 120 hrs MIC | 120 hrs MBC |
|---|---|---|---|---|
| C16 | 8 | 16 | 16 | 32 |
| C17 | 16 | 16 | 32 | 32 |

TABLE 4-continued

Inhibitory activity against *Liberibacter crescens.*

| | 24 hrs | | 120 hrs | |
|---|---|---|---|---|
| Compound | MIC | MBC | MIC | MBC |
| C18 | 8 | 8 | 16 | 16 |
| C19 | 8 | 8 | 16 | 16 |
| C20 | 16 | 16 | 32 | 32 |
| SSC8 | 16 | 16 | 32 | 32 |
| SSC11 | 16 | 16 | 32 | 32 |
| SA1 | 16 | 16 | 32 | 32 |
| SA2 | 16 | 16 | 32 | 32 |
| SA3 | 8 | 16 | 16 | 32 |
| SA4 | 16 | 32 | 32 | 64 |
| SA5 | 8 | 16 | 16 | 32 |
| SA6 | 16 | 16 | 32 | 64 |
| SA7 | 16 | 16 | 32 | 32 |
| SA8 | 16 | 16 | 32 | 32 |
| SA9 | 16 | 16 | 32 | 64 |
| Streptomycin | 16 | 16 | 32 | 32 |
| Oxytetracycline | | | 8 | 8 |

TABLE 5

Inhibitory activity against *Rhizobium etli.*

| | 24 hrs | | 120 hrs | |
|---|---|---|---|---|
| Compound | MIC | MBC | MIC | MBC |
| C16 | 16 | 16 | 32 | 32 |
| C17 | 32 | 64 | 32 | 64 |
| C18 | 16 | 16 | 32 | 32 |
| C19 | 32 | 32 | 32 | 64 |
| C20 | 32 | 64 | 32 | 64 |
| SSC8 | 16 | 32 | 32 | 64 |
| SSC11 | 16 | 32 | 32 | 64 |
| SA1 | 16 | 32 | 32 | 64 |
| SA2 | 16 | 32 | 32 | 64 |
| SA3 | 32 | 32 | 64 | 64 |
| SA4 | 8 | 16 | 16 | 32 |
| SA5 | 16 | 16 | 32 | 32 |
| SA6 | 32 | 32 | 64 | 64 |
| SA7 | 16 | 16 | 32 | 32 |
| SA8 | 8 | 16 | 16 | 32 |
| SA9 | 8 | 16 | 16 | 32 |
| Streptomycin | 4 | 4 | 16 | 16 |
| Oxytetracycline | 4 | 4 | 4 | 4 |

TABLE 6

Inhibitory activity against *Bradyrhizobium japonicum.*

| | 24 hrs | | 120 hrs | |
|---|---|---|---|---|
| Compound | MIC | MBC | MIC | MBC |
| C16 | 16 | 16 | 32 | 32 |
| C17 | 16 | 32 | 32 | 64 |
| C18 | 8 | 8 | 16 | 16 |
| C19 | 32 | 32 | 64 | 64 |
| C20 | 16 | 32 | 16 | 64 |
| SSC8 | 8 | 16 | 16 | 32 |
| SSC11 | 16 | 16 | 32 | 32 |
| SA1 | 16 | 16 | 32 | 32 |
| SA2 | 32 | 64 | 64 | 128 |
| SA3 | 16 | 32 | 32 | 64 |
| SA4 | 8 | 16 | 16 | 16 |
| SA5 | 16 | 16 | 32 | 32 |
| SA6 | 16 | 32 | 32 | 32 |
| SA7 | 32 | 32 | 32 | 32 |
| SA8 | 8 | 16 | 32 | 32 |

TABLE 6-continued

Inhibitory activity against *Bradyrhizobium japonicum.*

| | 24 hrs | | 120 hrs | |
|---|---|---|---|---|
| Compound | MIC | MBC | MIC | MBC |
| SA9 | 16 | 32 | 32 | 64 |
| Streptomycin | 32 | 32 | 32 | 32 |
| Oxytetracycline | 4 | 4 | 4 | 4 |

TABLE 7

Inhibitory activity against *Xanthomonas citri.*

| Compound | MIC | MBC |
|---|---|---|
| C16 | 16 | 32 |
| C17 | 16 | 32 |
| C18 | 16 | 32 |
| C19 | 32 | 64 |
| C20 | 16 | 32 |
| SSC8 | 32 | 64 |
| SSC11 | 32 | 64 |
| SA1 | 64 | 128 |
| SA2 | 32 | 64 |
| SA3 | 64 | 128 |
| SA4 | 32 | 64 |
| SA5 | 64 | 128 |
| SA6 | 64 | 128 |
| SA7 | 32 | 64 |
| SA8 | 32 | 64 |
| SA9 | 32 | 64 |
| SW-KC | 32 | 32 |
| Streptomycin | 32 | 32 |

TABLE 8

Inhibitory activity against *Mesorhizobium loti.*

| Compound | MIC | MBC |
|---|---|---|
| C16 | 8 | 16 |
| C17 | 16 | 32 |
| C18 | 16 | 32 |
| C19 | 16 | 32 |
| C20 | 8 | 16 |
| SSC8 | 16 | 32 |
| SSC11 | 16 | 32 |
| SA1 | 16 | 32 |
| SA2 | 16 | 32 |
| SA3 | 16 | 32 |
| SA4 | 16 | 32 |
| SA5 | 16 | 32 |
| SA6 | 16 | 32 |
| SA7 | 16 | 32 |
| SA8 | 16 | 32 |
| SA9 | 16 | 32 |
| Streptomycin | 16 | 32 |

TABLE 9

Inhibitory activity against *Sinorhizobium meliloti.*

| Compound | MIC | MBC |
|---|---|---|
| C16 | 32 | 64 |
| C17 | 16 | 32 |
| C18 | 32 | 64 |
| C19 | 32 | 64 |

TABLE 9-continued

| Inhibitory activity against *Sinorhizobium meliloti*. | | |
|---|---|---|
| Compound | MIC | MBC |
| C20 | 16 | 16 |
| SSC8 | 16 | 32 |
| SSC11 | 32 | 64 |
| SA1 | 16 | 32 |
| SA2 | 16 | 32 |
| SA3 | 32 | 64 |
| SA4 | 32 | 64 |
| SA5 | 32 | 64 |
| SA6 | 32 | 32 |
| SA7 | 16 | 32 |
| SA8 | 16 | 32 |
| SA9 | 16 | 32 |
| Streptomycin | 64 | 128 |

TABLE 10

| Inhibitory activity against *Agrobacterium tumefaciens*. | | |
|---|---|---|
| Compound | MIC | MBC |
| C16 | 64 | 128 |
| C17 | 64 | 64 |
| C18 | 32 | 128 |
| C19 | 32 | 128 |
| C20 | 32 | 128 |
| SSC8 | 32 | 64 |
| SSC11 | 32 | 128 |
| SA1 | 32 | 64 |
| SA2 | 32 | 64 |
| SA3 | 32 | 64 |
| SA4 | 16 | 64 |
| SA5 | 32 | 64 |
| SA6 | 16 | 64 |
| SA7 | 16 | 64 |
| SA8 | 32 | 128 |
| SA9 | 32 | 64 |
| Streptomycin | 64 | 128 |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Leonard M T, Fagen J R, Davis-Richardson A G, Davis M J, Triplett E W (2012) Complete genome sequence of *Liberibacter crescens* BT-1. Standards Genomic Sci. 7: 271-283.
2. Andrews, J M (2001) Determination of minimum inhibitory concentrations. Journal of Antimicrobial Chemotherapy 48, Suppl. S1, 5-16.
3. Wallace J R., R J, Nash, D R, Steele, L C and Steingrube, V (1986) Susceptibility testing of slowly growing mycobacteria by a microdilution MIC method with 7H9 broth. Journal of Clinical Microbiology, 24, 976-981.
4. Barloy-Hubler, F, Chéron, A, Hellégouarch, A and Galibert, F (2004) MSmc01944, a secreted peroxidase induced by oxidative stresses in *Sinorhizobium meliloti* 1021. Microbiology 150 657-664.
5. Dombrecht, B, Heusdens, C, Beullens, S, Verreth, C, Mulkers, E, Proost, P, Vanderleyden, J and Michiels, J (2005) Defence of *Rhizobium etli* bacteroids against oxidative stress involves a complexly regulated atypical 2-Cys peroxiredoxin. Molecular Microbiology 55, 1207-1221.
6. Fagen J R, Leonard M T, McCullough C M, Edirisinghe J N, Henry C S, et al. (2014) Comparative genomics of cultured and uncultured strains suggests genes essential for free-living growth of *Liberibacter*. PLoS ONE 9(1): e84469, doi:10.1371/journal.pone.0084469.
7. Shah, R and Emerich, D W (2006) Isocitrate dehydrogenase of *bradyrhizobium japonicum* is not required for symbiotic nitrogen fixation with soybean. Journal of Bacteriology 188:7600-7608.
8. Hanyu, M, Fujimoto, H, Tejima, k and Saekil, K (2009) Functional differences of two distinct catalases in *Mesorhizobium loti* MAFF303099 under free-living and symbiotic conditions. Journal of Bacteriology 191: 1463-1471
9. C. Silva, L. O. Regasini, M. S. Petrônio, D. H. S. Silva, V. S Bolzani, J. Belasque Jr., L. V. S. Sacramento and H. FerreiraAntibacterial (2013) Activity of alkyl gallates against *Xanthomonas citri* subsp. *citri* Journal of Bacteriology 195: 85-94 DOI: 10.1128/JB.01442-12.
10. Chilton, M, Currier, T C, Farrand, S K, Bendich A J, Gordon, M P and Nester, E W (1974) *Agrobacterium tumefaciens* DNA and PS8 Bacteriophage DNA Not Detected in Crown Gall Tumors Proc. Nat. Acad. Sci. USA 71: 3672-3676.
11. Lin, L, Lin C, Lin Y, Lin H, Shih, C, Chen, C, Huang, R and Kuo T (2010) Revisiting with a relative-density calibration approach the determination of growth rates of microorganisms by use of optical density data from liquid cultures. APPLIED AND ENVIRONMENTAL MICROBIOLOGY, 76:1683-1685.
12. Jorgensen, J H and Ferraro, MJ (2009) Antimicrobial susceptibility testing: A review of general principles and contemporary practices. Clinical Infectious Diseases 49:1749-55.
13. Taylor, PC, Schoenknecht, FD, Sherris, J C and Linner, EC (1983) Determination of minimum bactericidal concentrations of oxacillin for *Staphylococcus aureus*: influence and significance of technical factors. Antimicrobial Agents and Chemotherapy 23:142-150.

We claim:

1. A method of treating or preventing plant disease comprising administering to a plant in need thereof a composition comprising an effective amount of a SecA inhibiting compound selected from the group consisting of: N-(5-ethyl-1,3,4-thiadiazol-2-yl)-1-methyl-9H-beta-carboline-3-carboxamide (C16); 3-amino-6-phenyl-4-(3,4,5-trimethoxyphenyl)thieno[2,3-b]pyridine-2-carboxylic acid (C17); N-(1-{[(4-methoxyphenyl)amino]carbonyl}cyclohexyl)-4-(1H-tetrazol-1-yl)benzamide (C18); N-(6-methoxy-1,3-benzothiazol-2-yl)-2-[(5-methyl-1H-benzimidazol-2-yl)thio] acetamide (C19); and 7-benzoyl-11-(2-thienyl)-2,3,4,5,10,11-hexahydro-1H-diabenzo[b,e][1,4]diazepin-1-one (C20).

2. The method of claim 1, wherein the composition is administered to the plant by a method selected from the group consisting of dusting, sprinkling, spraying, brushing, dipping, smearing, impregnating, injection of the composition into plant vasculature, and application to a root system.

3. The method of claim 2, wherein the composition is administered to the plant by injecting the composition into plant vasculature or by application to a root system.

4. The method of claim 1, wherein the method is practiced in conjunction with application of a fertilizer.

5. The method of claim 1, wherein the plant disease is caused by *Candidatus liberibacter asiaticus*.

6. The method of claim 1, wherein the concentration of the SecA inhibiting compound in the composition is between about 100 μM and 1 mM.

7. The method, according to claim 1, wherein said compound is N-(5-ethyl-1,3,4-thiadiazol-2-yl)-1-methyl-9H-beta-carboline-3-carboxamide (C16).

8. The method, according to claim 1, wherein said compound is 3-amino-6-phenyl-4-(3,4,5-trimethoxyphenyl) thieno[2,3-b]pyridine-2-carboxylic acid (C17).

9. The method, according to claim 1, wherein said compound is N-(1-{[(4-methoxyphenyl)amino] carbonyl}cyclohexyl)-4-(1H-tetrazol-1-yl)benzamide (C18).

10. The method, according to claim 1, wherein said compound is N-(6-methoxy-1,3-benzothiazol-2-yl)-2-[(5-methyl-1H-benzimidazol-2-yl)thio]acetamide (C19).

11. The method, according to claim 1, wherein said compound is 7-benzoyl-11-(2-thienyl)-2,3,4,5,10,11-hexahydro-1H-diabenzo[b,e][1,4]diazepin-1-one (C20).

12. A method of treating or preventing plant disease comprising administering to a plant in need thereof a composition comprising an effective amount of a SecA inhibiting compound selected from the group consisting of: N-(4-methoxyphenyl)-N-{1-[(4-methoxyphenyl)carbamoyl]cyclohexyl}-4-(1H-tetrazol-1-yl)benzamide (SSC8); N-(4-methoxyphenyl)-N-{1-[(2-methylphenyl)carbamoyl] cyclohexyl}-4-(1H-tetrazol-1-yl)benzamide (SSC11); 2,6-Difluoro-N-[(2S)-3-methyl-1-oxo-1-{[4-(1H-tetrazol-1-yl) phenyl]amino}-2-butanyl]benzamide (SA1); 3-Amino-4-(4-fluorophenyl)-6-phenylthieno[2,3-b]pyridine-2-carboxylic acid (SA2); N-[(2S)-3-Methyl-1-oxo-1-{[3-(1H-tetrazol-1-yl)phenyl]amino}-2-butanyl]benzamide (SA3); (11S)-7-Benzoyl-11-phenyl-2,3,4,5,10,11-hexahydro-1H-dibenzo[b, e][1,4]diazepin-1-one (SA4); 7-Benzoyl-11-(4-methoxyphenyl)-3-phenyl-2,3,4,5,10,11-hexahydro-1H-dibenzo[b,e][1,4]diazepin-1-one (SA5); 7-Benzoyl-11-(4-hydroxyphenyl)-3-phenyl-2,3,4,5,10,11-hexahydro-1H-dibenzo[b,e][1,4]diazepin-1-one (SA6); 7-Benzoyl-11-(4-ethoxyphenyl)-2,3,4,5,10,11-hexahydro-1H-dibenzo[b,e][1, 4]diazepin-1-one (SA7); 7-Benzoyl-3-phenyl-11-(2-thienyl)-2,3,4,5,10,11-hexahydro-1H-dibenzo[b,e][1,4] diazepin-1-one (SA8); and 11-(4-hydroxy-3,5-dimethylphenyl)-3,3-dimethyl-7-(phenylcarbonyl)-2,3,4,5, 10,11-hexahydro-1H-dibenzo[b,e][1,4]diazepin-1-one (SA9).

13. The method of claim 12, wherein the composition is administered to the plant by a method selected from the group consisting of dusting, sprinkling, spraying, brushing, dipping, smearing, impregnating, injection of the composition into plant vasculature, and application to a root system.

14. The method of claim 13, wherein the composition is administered to the plant by injecting the composition into plant vasculature or by application to a root system.

15. The method of claim 12, wherein the method is practiced in conjunction with application of a fertilizer.

16. The method of claim 12, wherein the plant disease is caused by *Candidatus liberibacter asiaticus*.

17. The method of claim 12, wherein the concentration of the SecA inhibiting compound in the composition is between about 100 μM and 1 mM.

18. The method, according to claim 12, wherein said compound is N-(4-methoxyphenyl)-N-{1-[(4-methoxyphenyl)carbamoyl]cyclohexyl}-4-(1H-tetrazol-1-yl)benzamide (SSC8).

19. The method, according to claim 12, wherein said compound is N-(4-methoxyphenyl)-N-{1-[(2-methylphenyl)carbamoyl]cyclohexyl}-4-(1H-tetrazol-1-yl)benzamide (SSC11).

20. The method, according to claim 12, wherein said compound is 2,6-Difluoro-N-[(2S)-3-methyl-1-oxo-1-{[4-(1H-tetrazol-1-yl)phenyl]amino}-2-butanyl]benzamide (SA1).

21. The method, according to claim 12, wherein said compound is 3-Amino-4-(4-fluorophenyl)-6-phenylthieno [2,3-b]pyridine-2-carboxylic acid (SA2).

22. The method, according to claim 12, wherein said compound is N-[(2S)-3-Methyl-1-oxo-1-{[3-(1H-tetrazol-1-yl)phenyl]amino}-2-butanyl]benzamide (SA3).

23. The method, according to claim 12, wherein said compound is (11S)-7-Benzoyl-11-phenyl-2,3,4,5,10,11-hexahydro-1H-dibenzo[b,e][1,4]diazepin-1-one (SA4).

24. The method, according to claim 12, wherein said compound is 7-Benzoyl-11-(4-methoxyphenyl)-3-phenyl-2, 3,4,5,10,11-hexahydro-1H-dibenzo[b,e][1,4]diazepin-1-one (SA5).

25. The method, according to claim 12, wherein said compound is 7-Benzoyl-11-(4-hydroxyphenyl)-3-phenyl-2, 3,4,5,10,11-hexahydro-1H-dibenzo[b,e][1,4]diazepin-1-one (SA6).

26. The method, according to claim 12, wherein said compound is 7-Benzoyl-11-(4-ethoxyphenyl)-2,3,4,5,10,11-hexahydro-1H-dibenzo[b,e][1,4]diazepin-1-one (SA7).

27. The method, according to claim 12, wherein said compound is 7-Benzoyl-3-phenyl-11-(2-thienyl)-2,3,4,5,10, 11-hexahydro-1H-dibenzo[b,e][1,4]diazepin-1-one (SA8).

28. The method, according to claim 12, wherein said compound is 11-(4-hydroxy-3,5-dimethylphenyl)-3,3-dimethyl-7-(phenylcarbonyl)-2,3,4,5,10,11-hexahydro-1H-dibenzo[b,e][1,4]diazepin-1-one (SA9).

* * * * *